(12) United States Patent
Lau et al.

(10) Patent No.: US 8,057,391 B2
(45) Date of Patent: Nov. 15, 2011

(54) APPARATUS FOR DELIVERING HIGH INTENSITY FOCUSED ULTRASOUND ENERGY TO A TREATMENT SITE INTERNAL TO A PATIENT'S BODY

(75) Inventors: Michael Lau, Edmonds, WA (US); Shahram Vaezy, Seattle, WA (US); Alexander Lebedev, Seattle, WA (US); Michael J. Connolly, Bothell, WA (US)

(73) Assignee: Mirabilis Medica, Inc., Bothell, WA (US)

( * ) Notice: Subject to any disclaimer, the term of this patent is extended or adjusted under 35 U.S.C. 154(b) by 35 days.

(21) Appl. No.: 12/333,252

(22) Filed: Dec. 11, 2008

(65) Prior Publication Data
US 2009/0088636 A1  Apr. 2, 2009

Related U.S. Application Data

(62) Division of application No. 11/623,705, filed on Jan. 16, 2007, now abandoned.

(60) Provisional application No. 60/758,797, filed on Jan. 13, 2006.

(51) Int. Cl.
*A61B 8/00* (2006.01)
(52) U.S. Cl. ................... 600/439; 601/1; 601/2
(58) Field of Classification Search .......... 600/437–469, 600/473–476; 601/1–2
See application file for complete search history.

(56) References Cited

U.S. PATENT DOCUMENTS

| | | |
|---|---|---|
| 3,470,868 A | 10/1969 | Krause |
| 3,480,002 A | 11/1969 | Flaherty |
| 3,676,584 A | 7/1972 | Plakas |
| 3,941,112 A | 3/1976 | Habert |
| 4,059,098 A | 11/1977 | Murdock |

(Continued)

FOREIGN PATENT DOCUMENTS

EP 0301360 B1 2/1989

(Continued)

OTHER PUBLICATIONS

Cain, C.A., and S.-I. Umemura, "Concentric-Ring and Sector-Vortex Phased-Array Applicators for Ultrasound Hyperthermia," IEEE Transactions on Microwave Theory and Techniques 34(5):542-551, May 1986.

(Continued)

*Primary Examiner* — Sanjay Cattungal
(74) *Attorney, Agent, or Firm* — Christensen O'Connor Johnson Kindness PLLC

(57) ABSTRACT

An apparatus for delivering HIFU energy may include a probe with a plurality of leaves that provide a bowl-shaped HIFU therapy transducer. In once case, pins may slide within grooves in the leaves to deploy the leaves. In another case, spines may be configured to slide in a channel defined in each leaf. In other cases, a spring or a shape memory alloy may be used to deploy the leaves. In another implementation, a probe may be fitted with a flexible material that couples the HIFU therapy transducer to the probe and allows the transducer to be drawn to the side of the probe for insertion. In another implementation, a probe may have one or more inflatable bladders that form the HIFU therapy transducer. In yet another implementation, a probe may have an imaging component and a HIFU therapy transducer disposed thereon that rotate, as a unit, about a hinge.

20 Claims, 11 Drawing Sheets

U.S. PATENT DOCUMENTS

| | | |
|---|---|---|
| 4,097,835 A | 6/1978 | Green |
| 4,185,502 A | 1/1980 | Frank |
| 4,282,755 A | 8/1981 | Gardineer |
| 4,347,850 A | 9/1982 | Kelly-Fry |
| 4,484,569 A | 11/1984 | Driller |
| 4,742,829 A | 5/1988 | Law |
| 4,756,313 A | 7/1988 | Terwilliger |
| 4,835,689 A | 5/1989 | O'Donnell |
| 4,858,613 A | 8/1989 | Fry |
| 4,865,042 A | 9/1989 | Umemura |
| 4,893,624 A | 1/1990 | Lele |
| 5,005,579 A | 4/1991 | Wurster |
| 5,036,855 A | 8/1991 | Fry |
| 5,080,101 A | 1/1992 | Dory |
| 5,080,102 A | 1/1992 | Dory |
| 5,080,660 A | 1/1992 | Buelna |
| 5,117,832 A | 6/1992 | Sanghvi |
| 5,234,429 A | 8/1993 | Goldhaber |
| 5,271,402 A | 12/1993 | Yeung |
| 5,391,140 A | 2/1995 | Schaetzle |
| 5,441,499 A | 8/1995 | Fritzsch |
| 5,471,988 A | 12/1995 | Fujio |
| 5,474,071 A * | 12/1995 | Chapelon et al. ............ 600/439 |
| 5,492,126 A * | 2/1996 | Hennige et al. ............ 600/439 |
| 5,520,188 A * | 5/1996 | Hennige et al. ............ 600/459 |
| 5,558,092 A | 9/1996 | Unger |
| 5,619,999 A | 4/1997 | Von Behren |
| 5,666,954 A | 9/1997 | Chapelon |
| 5,676,692 A * | 10/1997 | Sanghvi et al. ................ 606/27 |
| 5,720,287 A | 2/1998 | Chapelon |
| 5,762,066 A * | 6/1998 | Law et al. ............ 600/439 |
| 5,769,790 A | 6/1998 | Watkins |
| 5,810,007 A | 9/1998 | Holupka |
| 5,823,962 A * | 10/1998 | Schaetzle et al. ............ 600/439 |
| 5,882,302 A * | 3/1999 | Driscoll et al. ............ 600/371 |
| 5,976,092 A | 11/1999 | Chinn |
| 5,993,389 A * | 11/1999 | Driscoll et al. ............ 600/371 |
| 6,002,251 A | 12/1999 | Sun |
| 6,007,499 A * | 12/1999 | Martin et al. ............ 601/3 |
| 6,042,556 A * | 3/2000 | Beach et al. ............ 601/3 |
| 6,050,943 A | 4/2000 | Slayton |
| 6,071,239 A * | 6/2000 | Cribbs et al. ............ 600/439 |
| 6,083,159 A * | 7/2000 | Driscoll et al. ............ 600/371 |
| 6,126,607 A | 10/2000 | Whitmore, III |
| 6,196,972 B1 | 3/2001 | Moehring |
| 6,217,530 B1 | 4/2001 | Martin |
| 6,254,601 B1 | 7/2001 | Burbank |
| 6,267,734 B1 | 7/2001 | Ishibashi |
| 6,315,741 B1 | 11/2001 | Martin |
| 6,390,973 B1 * | 5/2002 | Ouchi ............ 600/113 |
| 6,425,867 B1 * | 7/2002 | Vaezy et al. ............ 600/439 |
| 6,432,067 B1 | 8/2002 | Martin |
| 6,451,013 B1 | 9/2002 | Bays |
| 6,461,314 B1 * | 10/2002 | Pant et al. ............ 601/2 |
| 6,488,639 B1 | 12/2002 | Ribault |
| 6,500,133 B2 | 12/2002 | Martin |
| 6,508,774 B1 * | 1/2003 | Acker et al. ............ 601/2 |
| 6,533,726 B1 * | 3/2003 | Lizzi et al. ............ 600/439 |
| 6,537,224 B2 | 3/2003 | Mauchamp |
| 6,602,251 B2 | 8/2003 | Burbank |
| 6,613,004 B1 | 9/2003 | Vitek |
| 6,626,855 B1 | 9/2003 | Weng |
| 6,633,658 B1 | 10/2003 | Dabney |
| 6,635,054 B2 * | 10/2003 | Fjield et al. ............ 606/27 |
| 6,645,162 B2 | 11/2003 | Friedman |
| 6,666,835 B2 | 12/2003 | Martin |
| 6,676,601 B1 | 1/2004 | Lacoste |
| 6,692,450 B2 | 2/2004 | Coleman |
| 6,716,184 B2 | 4/2004 | Vaezy |
| 6,719,694 B2 | 4/2004 | Weng |
| 6,740,082 B2 | 5/2004 | Shadduck |
| 6,764,488 B1 | 7/2004 | Burbank |
| 6,840,936 B2 | 1/2005 | Sliwa, Jr. |
| 6,936,046 B2 | 8/2005 | Hissong |
| 7,063,666 B2 | 6/2006 | Weng |
| 7,105,007 B2 | 9/2006 | Hibler |
| 7,175,596 B2 | 2/2007 | Vitek |
| 7,258,674 B2 | 8/2007 | Cribbs |
| 7,452,357 B2 | 11/2008 | Voegele |
| 7,470,241 B2 | 12/2008 | Weng |
| 7,473,224 B2 * | 1/2009 | Makin ............ 600/439 |
| 7,699,782 B2 | 4/2010 | Angelsen |
| 2001/0012934 A1 | 8/2001 | Chandrasekaran |
| 2002/0029036 A1 | 3/2002 | Goble |
| 2002/0065512 A1 * | 5/2002 | Fjield et al. ............ 606/27 |
| 2002/0120259 A1 | 8/2002 | Lettice |
| 2003/0004439 A1 | 1/2003 | Pant |
| 2003/0060736 A1 | 3/2003 | Martin |
| 2003/0233045 A1 | 12/2003 | Vaezy |
| 2004/0030269 A1 | 2/2004 | Horn |
| 2004/0082859 A1 * | 4/2004 | Schaer ............ 600/459 |
| 2004/0153126 A1 | 8/2004 | Okai |
| 2004/0242999 A1 | 12/2004 | Vitek |
| 2004/0243201 A1 | 12/2004 | Goldman |
| 2005/0038340 A1 | 2/2005 | Vaezy |
| 2005/0085726 A1 | 4/2005 | Lacoste |
| 2005/0101854 A1 | 5/2005 | Larson |
| 2005/0154431 A1 | 7/2005 | Quistgaard |
| 2005/0203399 A1 * | 9/2005 | Vaezy et al. ............ 600/439 |
| 2005/0256405 A1 | 11/2005 | Makin |
| 2005/0267454 A1 | 12/2005 | Hissong |
| 2006/0052701 A1 * | 3/2006 | Carter et al. ............ 600/439 |
| 2006/0264748 A1 | 11/2006 | Vaezy |
| 2007/0004984 A1 * | 1/2007 | Crum et al. ............ 600/471 |
| 2007/0066990 A1 | 3/2007 | Marsella |
| 2007/0194658 A1 | 8/2007 | Zhang |
| 2007/0197918 A1 | 8/2007 | Vitek |
| 2007/0238994 A1 | 10/2007 | Stecco |
| 2008/0039724 A1 | 2/2008 | Seip |
| 2008/0071165 A1 | 3/2008 | Makin |
| 2008/0086036 A1 | 4/2008 | Hartley |
| 2008/0125771 A1 | 5/2008 | Lau |
| 2008/0221647 A1 | 9/2008 | Chamberland |
| 2008/0281314 A1 | 11/2008 | Johnson |
| 2008/0319436 A1 | 12/2008 | Daniel |
| 2009/0036774 A1 | 2/2009 | Weng |
| 2009/0228001 A1 | 9/2009 | Pacey |
| 2009/0326420 A1 | 12/2009 | Moonen |

FOREIGN PATENT DOCUMENTS

| | | |
|---|---|---|
| EP | 0614651 A1 | 9/1994 |
| EP | 0734742 A2 | 10/1996 |
| EP | 1 726 267 A2 | 11/2006 |
| JP | 405023336 A | 2/1993 |
| WO | 93/17646 A2 | 9/1993 |
| WO | 94/27502 A1 | 12/1994 |
| WO | 95/20360 A1 | 8/1995 |
| WO | 97/00646 A1 | 1/1997 |
| WO | 01/71380 A2 | 9/2001 |
| WO | 2004/073524 A1 | 9/2004 |
| WO | 2005/000097 A2 | 1/2005 |
| WO | 2006097661 A1 | 9/2006 |

OTHER PUBLICATIONS

Chapelon, J.Y., et al., "The Feasibility of Tissue Ablation Using High Intensity Electronically Focused Ultrasound," Proceedings of the IEEE Ultrasonics Symposium 1993, Baltimore, Oct. 31-Nov. 3, 1993, pp. 1211-1214.

Chen, L., et al., "Effect of Blood Perfusion on the Ablation of Liver Parenchyma With High-Intensity Focused Ultrasound," Physics in Medicine and Biology 38(11):1661-1673, Nov. 1993.

Cheng, S.-Q., et al., "High-Intensity Focused Ultrasound in the Treatment of Experimental Liver Tumour," Journal of Cancer Research and Clinical Oncology 123(4):219-223, Apr. 1997.

Coad, J.E., "Thermal Fixation: A Central Outcome of Hyperthermic Therapies," Proceedings of the SPIE Conference on Thermal Treatment of Tissue: Energy Delivery and Assessment III 5698:15-22, San Jose, Calif., Jan. 23, 2005.

Delon-Martin, C., et al., "Venous Thrombosis Generation by Means of High-Intensity Focused Ultrasound," Ultrasound in Medicine & Biology 21(1):113-119, 1995.

Friedland, F., "Ultrasonic Therapy," American Journal of Nursing 59(9):1272-1275, Sep. 1959.

Fry, F.J., "Recent Bioeffects With Ultrasound on the Reproductive System and Solid Tumors," Journal of the Acoustical Society of America 63(Suppl. 1):513, May 1978.

Hallberg, L., et al., "Menstrual Blood Loss—A Population Study: Variation at Different Ages and Attempts to Define Normality," Acta Obstetricia et Gynecologica Scandinavica 45(3):320-351, 1966.

Lee, J.M., et al., "Comparison of Wet Radiofrequency Ablation With Dry Radiofrequency Ablation and Radiofrequency Ablation Using Hypertonic Saline Preinjection: Ex Vivo Bovine Liver," Korean Journal of Radiology 5(4):258-265, Dec. 2004.

Lee, J.M., et al., "Wet Radio-Frequency Ablation Using Multiple Electrodes: Comparative Study of Bipolar Versus Monopolar Modes in the Bovine Liver," European Journal of Radiology 54:408-417, Jun. 2005.

Orsini-Meinhard, K., "UW Tech-Transfer Program Putting Discoveries to Work," The Seattle Times, May 27, 2007, 8 pages.

Rabkin, B.A., et al., "Biological and Physical Mechanisms of HIFU-Induced Hyperecho in Ultrasound Images," Ultrasound in Medicine & Biology 32(11):1721-1729, Nov. 2006.

Sanghvi, N.T., et al., "High Intensity Focused Ultrasound (HIFU) for the Treatment of Rectal Tumors: A Feasibility Study," Proceedings of IEEE Ultrasonics Symposium 3:1895-1898, Cannes, France, Nov. 1-4, 1994.

"ThermoDox™ Animal Studies to Be Presented at 6th International Symposium on Therapeutic Ultrasound in Oxford, England," Aug. 30-Sep. 2, 2006, Celsion, Inc., <http://www.celsion.com/news/releasedetail.cfm> [retrieved Oct. 8, 2007], 2 pages.

"ThermoDox™ : Heat-Activated Liposome Drug," © 2007 Celsion, Inc., <http://www.celsion.com/products/ThermoDox.cfm> [retrieved Oct. 8, 2007], 3 pages.

Vaezy, S., et al., "Image-Guided Acoustic Therapy," Annual Review of Biomedical Engineering 3:375-390, Aug. 2001.

Winter, T.C., et al., "Focal Tumor Ablation: A New Era in Cancer Therapy," Ultrasound Quarterly 22(3):204-209, Sep. 2006.

Zanelli, C.I., et al., "Design and Characterization of a 10 cm Annular Array Transducer for High Intensity Focused Ultrasound (HIFU) Applications," Proceedings of the IEEE Ultrasonics Symposium 3:1887-1890, Cannes, France, Nov. 1-4, 1994.

Mittleman, R.S., et al., "Use of the Saline Infusion Electrode Catheter for Improved Energy Delivery and Increased Lesion Size in Radiofrequency Catheter Ablation," Pacing and Clinical Electrophysiology 18(5, Pt. 1):953-1081, May 1995.

International Search Report dated Jun. 26, 2009, in International Application No. PCT/US2008/082829, filed Nov. 7, 2008.

Daum, D.R., and K. Hynynen, "A 256-Element Ultrasonic Phased Array System for the Treatment of Large Volumes of Deep Seated Tissue," IEEE Transactions on Ultrasonics, Ferroelectrics, and Frequency Control 46(5):1254-1268, Sep. 1999.

Enholm, J.K., et al., "Improved Volumetric MR-HIFU Ablation by Robust Binary Feedback Control," IEEE Transactions on Biomedical Engineering 57(1):103-113, Jan. 2010.

Mougenot, C., et al., "Automatic Spatial and Temporal Temperature Control for MR-Guided Focused Ultrasound Using Fast 3D MR Thermometry and Multispiral Trajectory of the Focal Point, " Magnetic Resonance in Medicine 52:1005-1015, 2004.

Mougenot, C., et al., "Three-Dimensional Spatial and Temporal Temperature Control With MR Thermometry-Guided Focused Ultrasound (MRgHIFU)," Magnetic Resonance in Medicine 61:603-614, 2009.

Ngo, F.C., et al., "An Experimental Analysis of a Sector-Vortex Phased Array Prototype," Proceedings of the IEEE Ultrasonics Symposium, Montreal, Oct. 3-6, 1989, vol. 2, pp. 999-1002.

Rabkin, B.A., et al., "Hyperecho in Ultrasound Images of HIFU Therapy: Involvement of Cavitation," Ultrasound in Medicine and Biology 31(7):947-956, Jul. 2005.

Umemura, S.-I., and C.A. Cain, "Acoustical Evaluation of a Prototype Sector-Vortex Phased-Array Applicator," IEEE Transactions on Ultrasonics, Ferroelectrics, and Frequency Control 39(1):32-38, Jan. 1992.

Extended European Search Report mailed Feb. 26, 2010, issued in European Patent Application No. 07811847.8, filed Apr. 13, 2007, 7 pages.

International Search Report mailed May 11, 2010, issued in International Application No. PCT/US2009/059589, filed Oct. 5, 2009, 5 pages.

International Search Report and Written Opinion mailed May 18, 2010, issued in International Application No. PCT/US2009/053050, filed Aug. 6, 2009, 15 pages.

International Search Report and Written Opinion mailed Oct. 26, 2010, issued in International Application No. PCT/US2010/026565, filed Mar. 8, 2010, 10 pages.

* cited by examiner

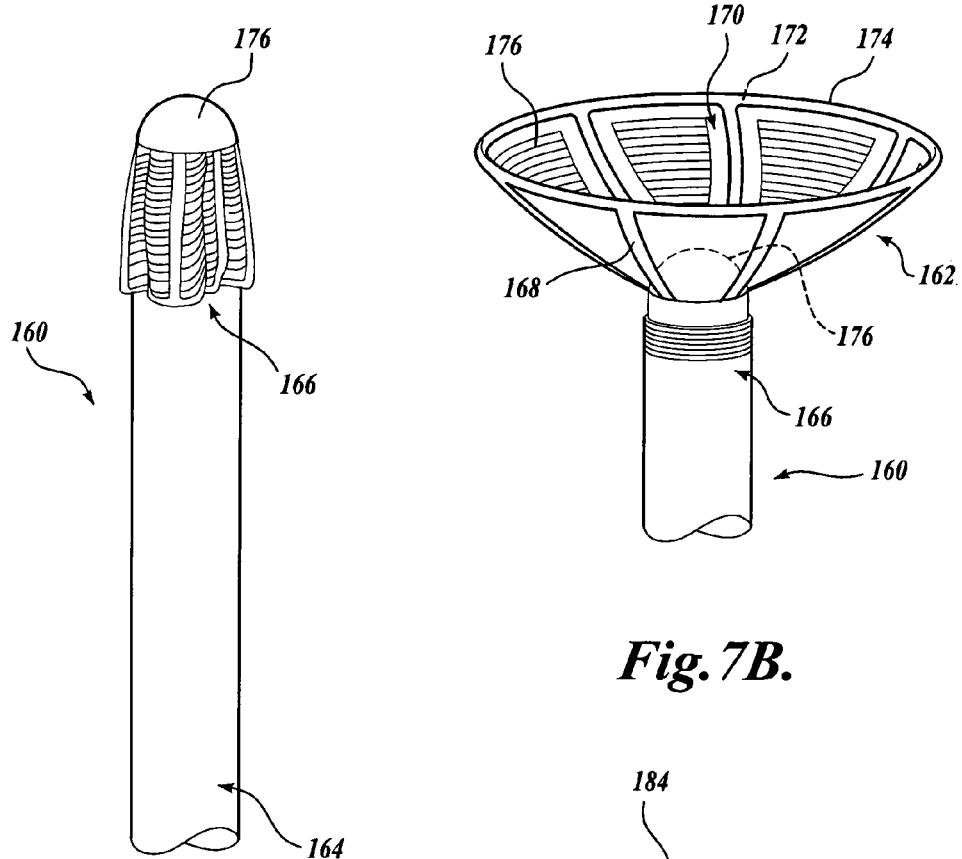
Fig. 7A.
Fig. 7B.
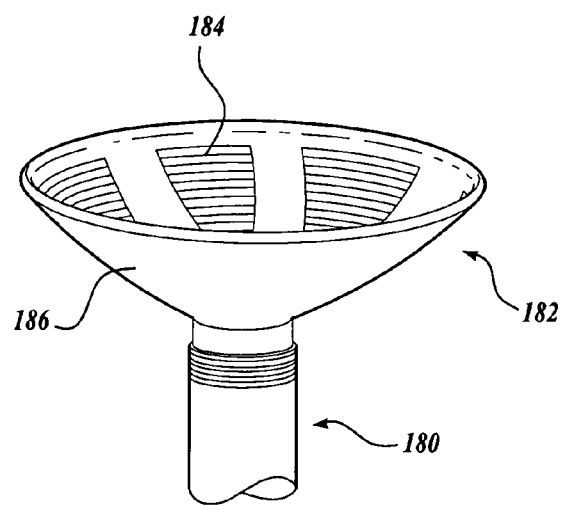
Fig. 8.

APPARATUS FOR DELIVERING HIGH INTENSITY FOCUSED ULTRASOUND ENERGY TO A TREATMENT SITE INTERNAL TO A PATIENT'S BODY

CROSS-REFERENCES TO RELATED APPLICATIONS

This application is a divisional of U.S. patent application Ser. No. 11/623,705, filed Jan. 16, 2007, which claims the benefit of U.S. Provisional Patent Application No. 60/758,797, filed Jan. 13, 2006, the disclosures of which are incorporated by reference herein in their entirety.

BACKGROUND

The present application is directed to apparatus that provide therapeutic treatment of internal pathological conditions using high-intensity focused ultrasound energy, and more particularly, to providing improved apparatus for insertion and deployment of a HIFU therapy transducer, with or without an imaging component.

Delivery of high-intensity focused ultrasound (HIFU) energy has emerged as a precise, non-surgical, minimally-invasive treatment for benign and malignant tumors. (See, e.g., S. Vaezy, M. Andrew, P. Kaczkowski et al., "Image-guided acoustic therapy," Annu. Rev. Biomed. Eng. 3, 375-90 (2001)). At focal intensities 4-5 orders of magnitude greater than diagnostic ultrasound (typically about 0.1 W/cm$^2$), HIFU (typically about 1000-10,000 W/cm$^2$) can induce lesions or tissue necrosis at a small location deep in tissue while leaving tissue between the ultrasound source and focus unharmed. Tissue necrosis is a result of focal temperatures typically exceeding 70° C. which can occur with relatively short intervals of HIFU exposure. HIFU is currently being used clinically for the treatment of prostate cancer and benign prostatic hyperplasia, as well as malignant bone tumor and soft tissue sarcoma. Clinical trials for HIFU treatment of breast fibroadenomas and various stage 4 primary and metastatic cancer tumors of the kidney and liver are underway.

Uterine fibroid, as an example of a pathological condition in the female pelvis, is the most common pelvic tumor in women of reproductive age. Uterine fibroids, or leiomyoma, are benign tumors that cause abnormal uterine bleeding. The incidence of fibroids has been estimated to be 20-25% in women in their reproductive years, although autopsy studies show an incidence upwards of 75%. Approximately ⅓ of these women will have a tumor that is symptomatic requiring treatment. HIFU energy delivered using a transvaginal transducer can provide a feasibly minimally-invasive treatment for uterine fibroids.

Further development of HIFU devices for providing therapy in obstetrics and gynecology, as well as other fields of medical endeavor, is desired. In particular, improved devices are needed which can provide noninvasive therapeutic treatment of uterine fibroids, recurrent leiomyosarcoma, and other solid tumors of the uterine corpus and cervix, as well as abnormal uterine bleeding conditions and many other obstetric and gynecologic pathological conditions.

A major challenge for transvaginal HIFU treatment of uterine pathologies is the deployment of a HIFU therapy transducer having an aperture of adequate size. In general, devices with a larger HIFU aperture tend to optimize the focal length of the HIFU beam and the therapeutic effect of the focused ultrasound energy. However, the size and configuration of the HIFU aperture are generally limited by the size and shape of the vaginal cavity and the location of the cervix and vaginal fornices.

Even more challenging is the issue of transvaginal insertion of a HIFU therapy transducer through the rather narrow vaginal introitus. The present application addresses the problems of insertion of a probe with a HIFU transducer through small passages, such as the vaginal introitus, and deployment of the HIFU transducer, with or without an imaging component, within a body cavity in order to achieve optimal imaging and HIFU therapeutic effects.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one implementation, an apparatus for delivering high intensity focused ultrasound (HIFU) energy to a treatment site internal to a patient's body may include an elongate probe with a HIFU therapy transducer coupled thereto. The HIFU therapy transducer is comprised of a plurality of leaves, each leaf having a front surface adapted to direct HIFU energy to a treatment site when the probe is inserted in a patient's body and a deployment mechanism is activated. When activated, the deployment mechanism is configured to deploy the leaves by directing the leaves in a radially outward direction. The leaves thus deployed collectively provide a bowl-shaped HIFU therapy transducer having an outer edge with a diameter that is larger than the diameter of the probe. To facilitate insertion of the probe in the patient's body, the plurality of leaves are configured to collapse when the deployment mechanism is not activated. The collapsed leaves occupy a space having a diameter smaller than the diameter of the outer edge of the HIFU therapy transducer when the leaves are deployed.

In one aspect, the probe may include a sleeve disposed around a shaft. The shaft is configured to slide within the sleeve from a retracted position to an extended position. Each leaf is coupled to a distal end of the shaft, and the deployment mechanism includes a pin coupled to the sleeve that slides within a groove defined in each leaf. Activation of the deployment mechanism comprises sliding the shaft within the sleeve toward the extended position, which causes each leaf to be pushed outward from the distal end of the sleeve. As the pin slides within the groove in each respective leaf, the distal end of the leaf is directed radially outward to a desired position to provide the bowl-shaped HIFU transducer. An actuator, such as a button connected to the shaft, may be configured to help drive the shaft between the retracted and extended positions.

In another aspect, each leaf may be coupled to a distal end of the sleeve, wherein the deployment mechanism of each leaf includes a spine coupled to the shaft. The spines are configured to slide within the sleeve into a channel defined in the leaf. Activation of the deployment mechanism comprises sliding the shaft within the sleeve toward the extended position, thus causing the spine for each leaf to be pushed into the channel of the respective leaf which directs the leaf radially outward. When the spines are retracted in the sleeve and the leaves are collapsed, the leaves are capable of being grouped together to occupy a space having a diameter that is equal to or smaller than the diameter of the sleeve.

In another aspect, the proximal end of each leaf may be coupled to a distal end of the shaft, wherein the deployment mechanism includes a spring having a first end coupled to the shaft and a second end disposed within the leaf. Activation of the deployment mechanism comprises sliding the shaft within the sleeve toward the extended position. As each leaf is pushed outward from the sleeve, the second end of the spring in each leaf biases the distal end of the leaf in a radially outward direction to provide the bowl-shaped HIFU transducer.

In another aspect, a portion of each leaf may be formed of an energy-activated shape memory alloy. The deployment mechanism includes a coupling of the shape memory alloy to an energy source. Activation of the deployment mechanism comprises delivering energy from the energy source to the shape memory alloy of each leaf to cause the shape memory alloy to take a predefined shape in which the distal end of the leaves are directed radially outward to provide the bowl-shaped HIFU transducer. The portion of the leaves formed of a shape memory alloy may be configured as a spine in each leaf.

The HIFU therapy transducer may also be coupled to the probe via a hinge, enabling the HIFU transducer to rotate about the hinge to help aim the HIFU energy toward the treatment site.

In another implementation, an apparatus for HIFU energy to a treatment site internal to a patient's body may include an elongate probe fitted with a flexible material that couples a HIFU therapy transducer to the probe. For reference purposes, the HIFU therapy transducer may be considered as having a major axis across its face. In a resting state, the flexible material deploys the transducer in a therapy position wherein the major axis of the transducer is non-parallel to the longitudinal axis of the probe. To facilitate insertion of the probe in the patient's body, the flexible material is configured to stretch and allow the transducer to be drawn to the side of the probe to an insertion position where the major axis of the transducer is generally parallel to the longitudinal axis of the probe. After insertion, the transducer is released and the flexible material returns toward its resting state, thus deploying the transducer for therapy delivery. If desired, an actuator may be coupled to the transducer and manipulated to draw the transducer to the side of the probe for insertion and/or removal of the probe from the patient. The actuator may also be manipulated to deploy the transducer for therapy delivery after the probe has been inserted in the patient.

In another implementation, an apparatus for delivering HIFU energy to a treatment site internal to a patient's body may include an elongate probe fitted with a flexible material that has one or more inflatable bladders. The bladders extend radially outward from the distal end of the probe. When inflated, the bladders form a HIFU therapy transducer having an aperture that is larger than the diameter of the probe. The bladders are not inflated until after the probe is inserted in the patient's body. When not inflated, the bladders occupy a space having a diameter smaller than the diameter of the HIFU therapy transducer when otherwise inflated. The flexible material is configured with a front surface that is adapted to direct HIFU energy to the treatment site when the bladders are inflated.

In one aspect, the bladders may comprise one or more inflatable channels that extend radially outward from the distal end of the probe, wherein the front face of the flexible material extends between the inflatable channels. The inflatable channels may terminate in an inflatable ring that forms an outer edge of the HIFU therapy transducer. When inflated, the diameter of the ring is larger than the diameter of the probe.

In another implementation, an apparatus for delivering image-guided HIFU energy to a treatment site internal to a patient's body may include a probe with a support structure having an imaging component and a HIFU therapy transducer disposed thereon. A hinge is used to connect the support structure to the distal end of the probe. The imaging component is preferably adapted for producing an image of a portion of the patient's body that includes the treatment site, while the HIFU therapy transducer directs HIFU energy to the treatment site. The HIFU therapy transducer is disposed on the support structure in defined relation to the imaging component.

To facilitate insertion of the probe in a patient's body, the support structure is capable of rotating about the hinge to a position generally parallel to the longitudinal axis of the probe. After insertion of the probe, the support structure is capable of rotating about the hinge to a position non-parallel to the longitudinal axis of the probe. The hinge thus provides an articulation that enables the imaging and therapy transducers as a unit to be positioned relative to the treatment site in the patient's body.

In one aspect, the HIFU therapy transducer may be bowl-shaped, with the imaging component disposed in the interior of the therapy transducer. In another aspect, the imaging component may be disposed on the support structure to the exterior of the HIFU therapy transducer.

In the foregoing implementations, an imaging component included with the probe may be configured to use reflected ultrasound energy to produce an image of a portion of the patient's body. Alternatively, or in addition, the imaging component may be configured to use reflected light to produce an image of a portion of the patient's body. Still another alternative is that the imaging component consists of the same transducer as used to produce the HIFU energy. In some cases, the image produced by the imaging component may include a portion of the HIFU therapy transducer and/or the focal point of the HIFU energy within the tissue. The image obtained by the imaging component may assist in positioning the HIFU therapy transducer within the patient's body and in monitoring the delivery and effects of the HIFU therapy at the treatment site.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 7A and 7B illustrate an implementation of the invention having a HIFU therapy transducer with an inflatable support;

FIG. 8 illustrates another implementation of a probe having a HIFU therapy transducer with an inflatable support;

DETAILED DESCRIPTION

Disclosed herein are implementations of an apparatus designed for delivering high-intensity focused ultrasound (HIFU) energy to a treatment site internal to a patient's body. The implementations herein facilitate the insertion of a probe with a HIFU therapy transducer through a narrow opening to various cavities of the human body. These implementations can be applied to body orifices and cavities including, but not limited to, the urinary tract, gastrointestinal tract, cardiovascular system, respiratory system, and reproductive system, as well as through endoscopes or laparoscopes for minimally-invasive surgery in various parts of the body. For purposes of illustration herein, various implementations are shown and discussed in the context of providing HIFU therapy in the female reproductive system.

Figure 1:
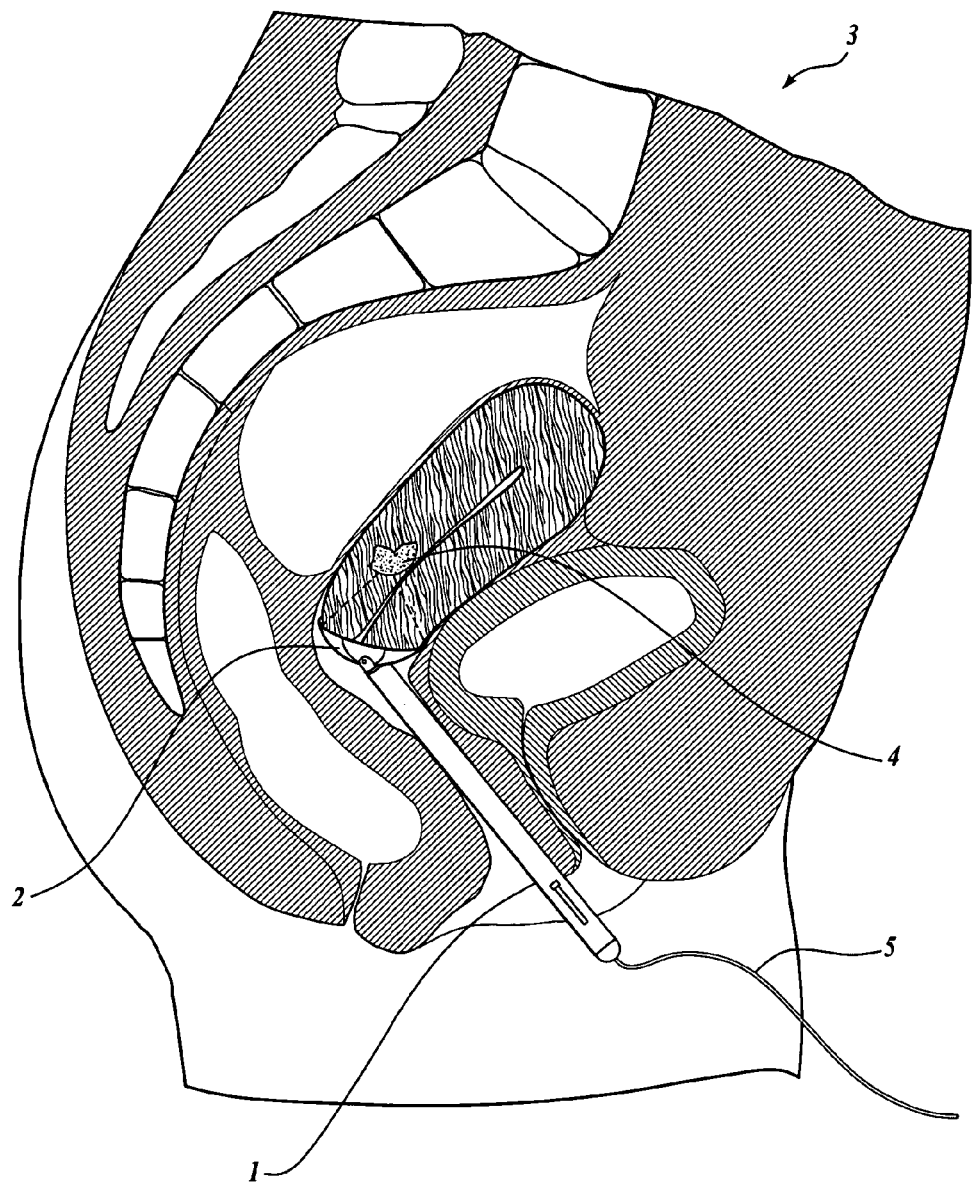
FIG. 1 illustrates in section view a possible environment in which an implementation of the present invention may be used for treatment of pathologies of the female reproductive system.

FIG. 1 illustrates an implementation of the invention, wherein a probe 1 with a HIFU therapy transducer 2 has been introduced into the vaginal cavity of a female patient 3. In this particular implementation, the HIFU therapy transducer is designed for coupling to the uterine cervix for delivering a highly focused beam of HIFU energy, depicted by dotted line, to a treatment site within the uterus. In this illustration, the treatment site is a uterine fibroid 4. By mating against the cervix, the HIFU therapy transducer 2 is able to direct ultrasound emissions that are limited to the uterine tissue, thereby enhancing the therapeutic, and possibly diagnostic, effects of the ultrasound energy by emitting the energy through a constant uterine tissue medium.

An additional coupling device can be used between the transducer 2 and the cervix to optimize the ultrasound transmission. The coupling may further include a cooling component. Known in the art are various pillows filled with fluid that can provide a cooled coupling between a HIFU transducer and a mass of tissue. The probe 1, shown in FIG. 1, further includes a coupling 5 to an external source that may deliver a circulation of cooling fluid, as well as energy to the probe 1 for operating the components of the probe. The cooling fluid is used to lower the temperature of the HIFU transducer as well as the tissue surrounding the transducer, including but not limited to the cervix, to decrease the risk of collateral thermal damage from the focused HIFU beam. The coupling of the transducer 2 to the cervix further enables the clinician to manipulate the position of the cervix and uterus to optimize the HIFU treatment.

As will be discussed with respect to the remaining figures, implementations of the invention are configured with a HIFU therapy transducer having a compact state for insertion into the vaginal cavity, after which the HIFU therapy transducer is deployed to a larger state in which the transducer can deliver HIFU therapy to target tissue in the body.

If desired, the probe 1 may further include an imaging component that is operable to visualize the various pelvic organs and pathologies. The imaging component may be designed to produce two-dimensional or three-dimensional visual images of the tissue of interest and/or blood flow of the tissue, as well as provide a temperature quantification of the tissue in view. Further, while the imaging system may be designed to use ultrasound energy, imaging technologies are not limited to such an energy modality.

As depicted, the therapeutic component of the HIFU transducer may be constructed with various configurations to achieve optimal focal length and aperture sizes and shapes to achieve an optimal energy delivery for therapeutic purposes. Implementations of the invention can be constructed, as described herein, to provide optimal energy delivery to intended targets, such as fibroid tumors in the uterus, while also addressing the issue of limiting any collateral damage to adjacent tissue. Furthermore, by managing the harmonics of transducer excitation, as well as the phase and direction of energy emission, the shape and location of the focal point of the HIFU transmission can be adjusted.

Elements for generating HIFU energy are well known in the art. A HIFU transducer may be configured with HIFU-generating element arranged in an annular array, for example, which may allows focal range control. Alternatively, the HIFU generating elements may be arranged in a linear array, which may allows both focal range and steering control. In yet other implementations, the elements could be arranged in a two-dimensional array, which may allow focal range and steering control in three dimensions. The latter arrangement is preferably used in concert with a two-dimensional imaging array that allows for three-dimensional ultrasound visualization. Where multiple elements are used, the elements may be phased with varying phase to allow proper focusing of the HIFU transducer on various targets in the body. Alternatively, HIFU emission from the multiple elements may be coordinated to produce a beam as if coming from a single element.

Figure 2:
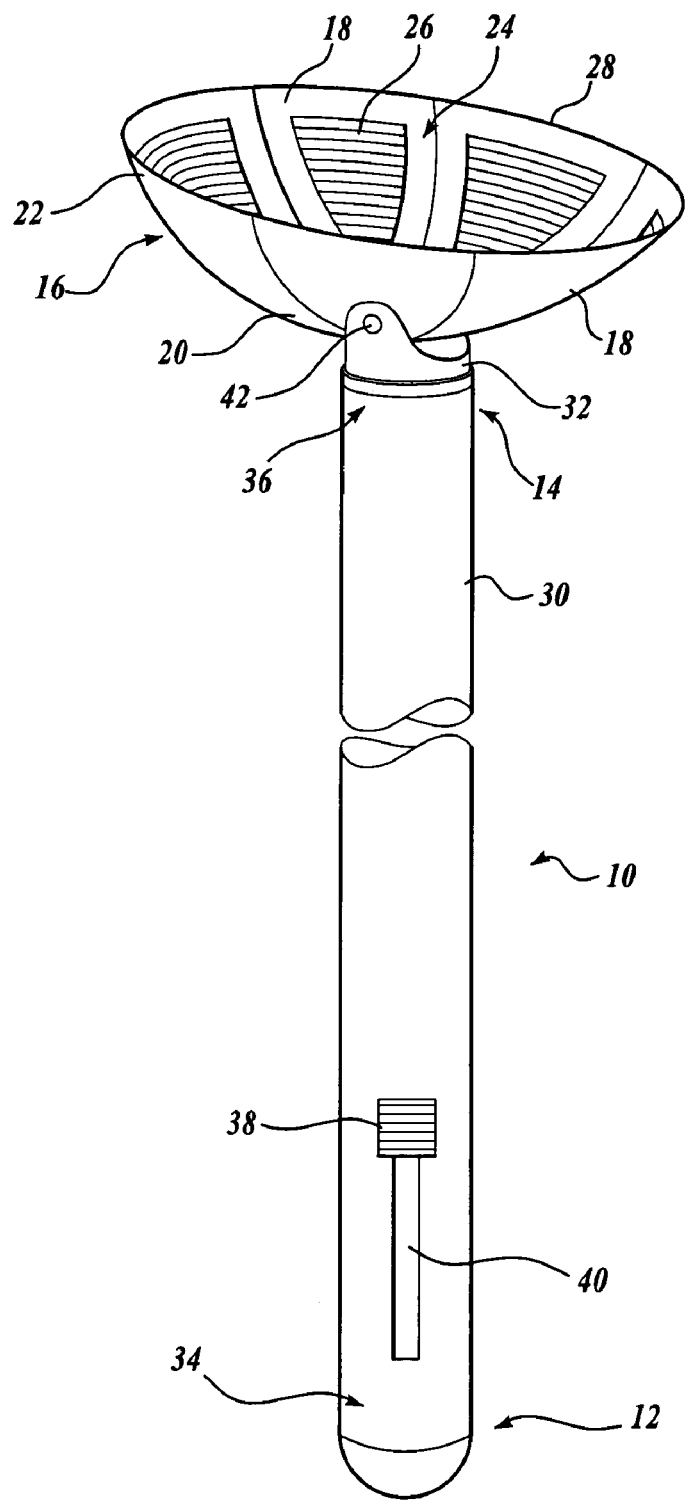
FIG. 2 illustrates the implementation of the apparatus depicted in FIG. 1.

An apparatus for delivering HIFU energy constructed in accordance with an implementation of the present invention, as shown in FIG. 1, is shown in greater detail in FIG. 2. The apparatus includes an elongate probe 10 having a proximal end 12 and a distal end 14. The proximal end 12 of the probe 10 preferably has a section adapted for positioning the distal end 14 at a desired location within a body cavity when the probe 10 is inserted through an orifice into the patient's body. In this implementation, the distal end 14 of the probe 10 has a HIFU therapy transducer 16 coupled thereto. The HIFU therapy transducer 16 comprises a plurality of leaves 18. Each leaf 18, as shown, has a proximal end 20 and a distal end 22, as well as a deployment mechanism that will be discussed in greater detail below. The proximal end 20 of each leaf 18 is coupled to the distal end 14 of the probe 10.

Each leaf 18 has a front surface 24 adapted to direct HIFU energy to a treatment site in the patient's body when the HIFU therapy transducer 16 is deployed. In the implementation shown in FIG. 2, the front surface 24 of at least one of the leaves includes an active element 26 disposed thereon. The active element 26 is operable to generate HIFU energy that is directed by the transducer 16 to the treatment site, such as the fibroid shown in FIG. 1. HIFU-generating elements, as well as the signals and systems required for operating the active elements to generate HIFU energy, are well known in the art and need not be discussed in detail herein. For example, HIFU elements using piezoelectric technologies are known in the art and may be used in the implementations discussed herein.

Depending on the materials used to construct the leaves 18 and the dimension of the leaves 18 in the HIFU therapy transducer 16, the leaves 18 may each be independently coupled to the probe 10, separate from one another. For stability of the transducer 16, the leaves 18 may also be interconnected to each other if desired. In FIG. 2, the leaves 18 are constructed to collapse to a smaller state by sliding over the top of one another, thus reducing the dimension of the HIFU therapy transducer from a deployed state, as shown in FIG. 2, to a more compact state that facilitates insertion of the probe 10 into a body cavity.

Each of the leaves 18 has a deployment mechanism that is used to deploy the HIFU therapy transducer 16 to a state as shown in FIG. 2 after the probe 10 is inserted into the patient. When activated, the deployment mechanism is configured to deploy the leaves 18 by directing the distal end 22 of the leaves 18 in a radially outward direction. The leaves, thus deployed, collectively provide a bowl-shaped HIFU therapy transducer 16 having an outer edge 28 with a diameter that is larger than the diameter of the probe 10. The HIFU therapy transducer 16, when deployed, has an aperture of a size sufficient to direct a highly focused beam of HIFU energy to a treatment site in a patient. When the deployment mechanism is not activated, the collapsed leaves 18 occupy a space having a diameter smaller than the diameter of the outer edge 28 of the transducer 16 when the leaves 18 are deployed.

In the implementation shown in FIG. 2, as well as certain other implementations disclosed herein, the probe 10 includes a sleeve 30 disposed around a shaft 32. The sleeve 30 has a proximal end 34, a distal end 36, and a longitudinal axis extending therebetween. The shaft 32 is configured to slide within the sleeve 30 from a retracted position to an extended position along the longitudinal axis of the probe 10.

To assist the sliding of the shaft from the retracted to the extended position, an actuator, such as a button 38, may be provided. In FIG. 2, the button 38 is connected to the shaft 32 and slides within a groove 40 in the sleeve 30. A clinician operating the probe may grasp the button 38 and slide it within the groove 40 to the position shown in FIG. 2 to place the shaft in the extended position.

When the button 38 is slid through the groove 40 toward the proximal end 34 of the probe, the shaft 32 is pulled within the sleeve 30. As the shaft 32 is sliding inward, the leaves 18 contact the distal end 36 of the sleeve 30 and inwardly contract to be pulled within the sleeve 30. In the implementation shown, a portion of each leaf 18 is designed to slide over in front of an adjacent leaf 18 as the shaft 32 is pulled within the sleeve 30 and the leaves 18 contract.

FIG. 2 additionally illustrates a hinge 42 at the distal end 14 of the probe 10. In this implementation, the HIFU therapy transducer 16 is coupled to the distal end 14 of the probe 10 via the hinge 42. The hinge 42 has an axis about which the transducer 16 can rotate to aim the HIFU energy toward the treatment site in the patient's body, e.g., as depicted in FIG. 1.

Figures 3A, 3B, 3C:
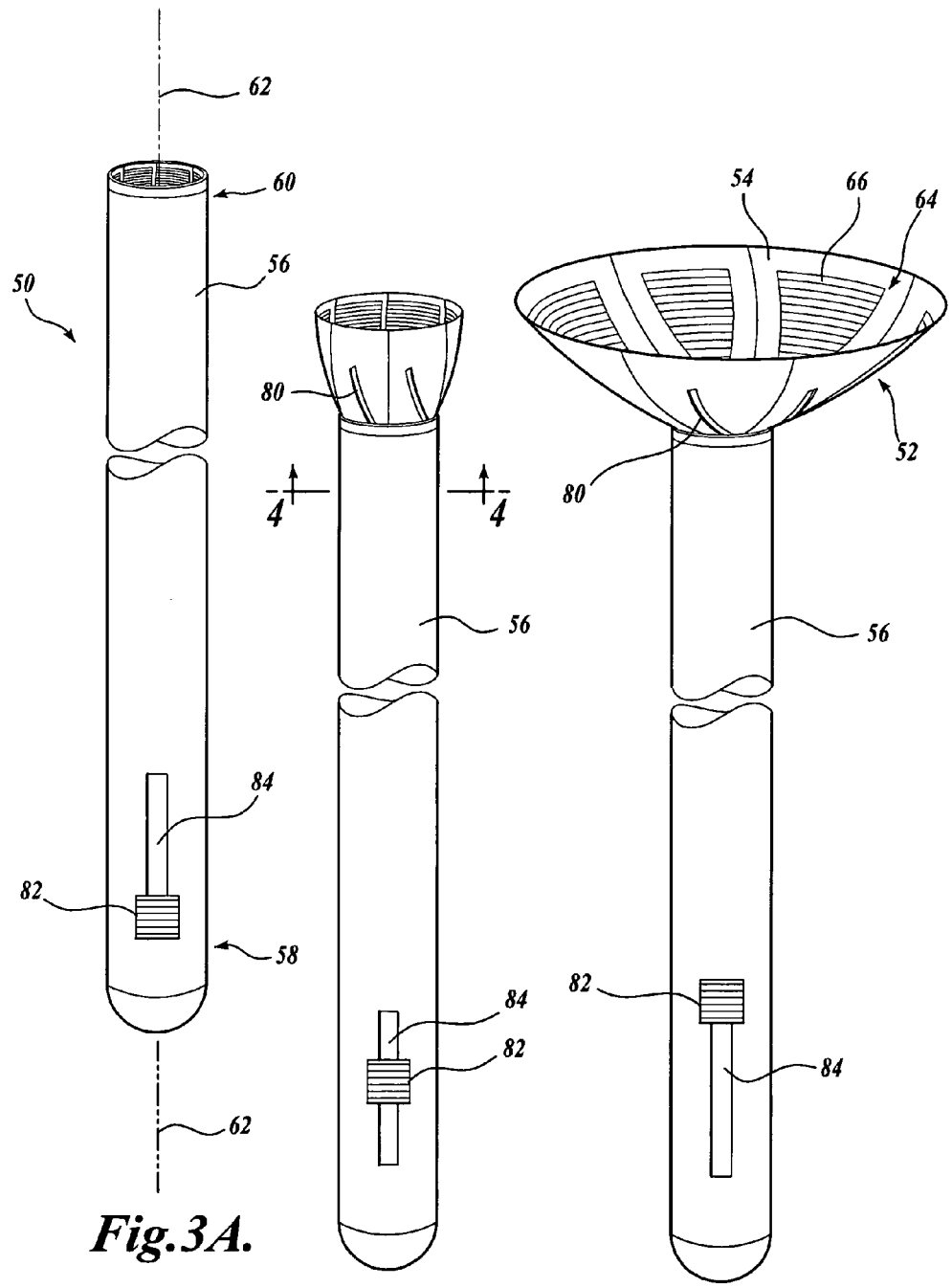
FIGS. 3A-3C illustrate an implementation of the invention having a retractable HIFU therapy transducer.

FIGS. 3A-3C illustrate an implementation of an elongate probe 50 having a HIFU therapy transducer 52 comprised of retractable leaves 54, similar to the probe 10 shown in FIGS. 1 and 2. The probe 50 includes a sleeve 56 disposed around a shaft 70 (FIG. 4) inside the sleeve. The sleeve 56 has a proximal end 58, a distal end 60, and a longitudinal axis 62 extending therebetween. The shaft is configured to slide inside the sleeve 56 from a retracted position, as shown in FIG. 3A, to an extended position, as shown in FIG. 3C, along the longitudinal axis 62. FIG. 3B illustrates the shaft at an intermediate stage between the retracted and extended positions.

As with the implementation shown in FIGS. 1 and 2, each leaf 54 has a front surface 64 adapted to direct HIFU energy to a treatment site when the probe 50 is inserted into a patient's body. An active element 66 disposed on the front surface 64 is operable to generate the HIFU energy that is directed to the treatment site. Although the implementation in FIGS. 3A-3C depicts multiple leaves 54 having a front surface 64 with an active element 66, not all of the leaves 54 are required to have an active element. Indeed, in at least some implementations, the front surface 64 may be designed without any active elements for generating HIFU energy. Instead, the front surface 64 of at least one of the leaves 54 is configured to reflect HIFU energy toward the treatment site, wherein the HIFU energy is received from a source that is remote from the leaf. For example, a HIFU energy source may be coupled to the probe at a location central to the HIFU therapy transducer 52 but away from the leaves 54. Alternatively, a HIFU energy source may be located separate from the probe 50. In either case, the front surface 64 of at least one of the leaves 54 is provided with a mirror-like material that reflects HIFU energy incident upon the surface 64. Materials with properties known for reflecting incident energy are readily available and recognized by persons having ordinary skill. The geometry of the leaves 54, when in a deployed state, is configured to direct the HIFU energy to a focal point at the intended treatment site in the patient.

Figure 4:
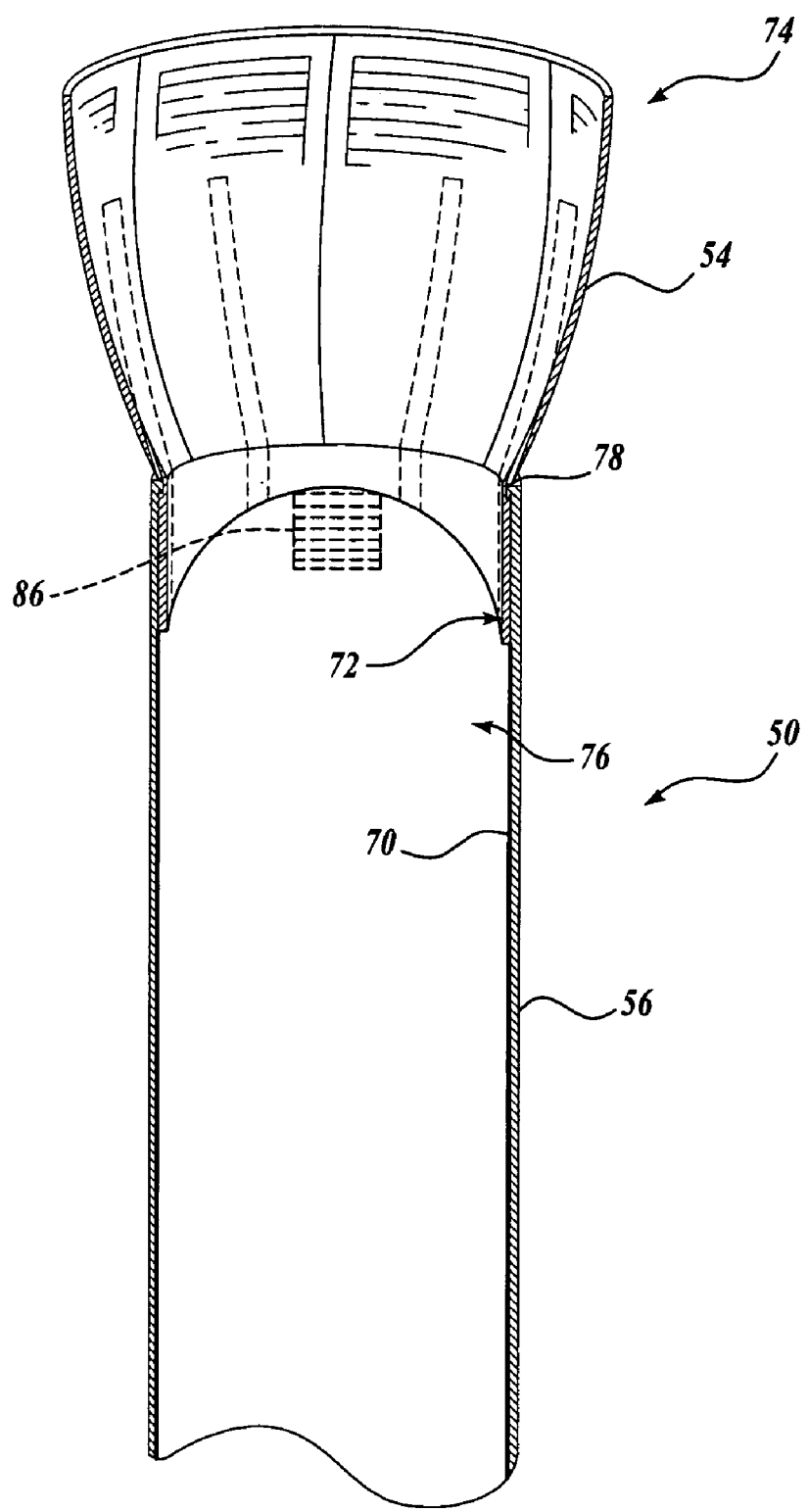
FIG. 4 illustrates a side section view of the implementation shown in FIGS. 3A-3C.

FIG. 4 illustrates a side section view of the probe 50 shown in FIG. 3B. In FIG. 4, the sleeve 56 is shown disposed around the shaft 70. Each of the leaves 54 has a proximal end 72 and a distal end 74. The proximal end 72 of each leaf 54 is coupled to a distal end 76 of the shaft 70, e.g., through a pin, adhesive, welding, or the like. Where the leaf 54 includes an active HIFU-generating element, the coupling further includes a means for conveying energy from the probe 50 to the active element, such as a wire.

Each leaf 54 further includes a deployment mechanism that, when activated, deploys the leaves 54 by directing the distal end 72 of the leaves in a radially outward direction. In the implementation shown in FIGS. 3A-3C and in FIG. 4, the deployment mechanism of each leaf includes a pin 78 that is coupled to the distal end 60 of the sleeve 56. The pin 78 is configured to slide within a groove 80 (FIGS. 3B and 3C) defined in the leaves 54.

Activation of the deployment mechanism in this implementation comprises sliding the shaft 70 within the sleeve 56 toward the extended position shown in FIG. 3C. As the shaft 70 slides upward through the sleeve 56, each leaf 54 is pushed outward from the distal end 60 of the sleeve 56. As each leaf is pushed outward, the pin 78 for each respective leaf 54 slides within the groove 80 to direct the distal end 74 of the leaf radially outward to a desired position in which the leaves collectively provide a bowl-shaped HIFU transducer 52, as shown in FIG. 3C.

In the illustrated implementation, the grooves 80 are defined at an angle relative to the longitudinal axis 62 such that the leaves 54 are directed sideways, as well as outward, when the shaft 70 is slid to the extended position. Similarly, when the shaft 70 is drawn to the retracted position shown in FIG. 3A, the pin 78 for each leaf 54 slides within the groove 80 to guide the leaf laterally and radially inward as the leaves are pulled into the sleeve 56. As depicted in FIG. 3B, at least a portion of a leaf 54 in the plurality of leaves is configured to overlap at least a portion of another leaf 54 when the leaves are retracted and held within the sleeve 56. To assist with retracting or extending the shaft 70, an actuator, such as a button 82, may be attached to the shaft 70, as shown in FIGS. 3A-3C. As with the implementation shown in FIGS. 1 and 2, the button 82 may slide within a groove 84 defined in the sleeve 56. A force exerted on the button 82 in a direction toward or away from the distal end 60 of the sleeve 56 is translated to the shaft 70 for moving the shaft 70 within the sleeve.

If desired, the pin 78 may include a detent that is configured to secure the pin within the groove 80 in each respective leaf. Furthermore, if desired, the probe 50 may be configured such that the distal end 76 of the shaft 70 extends beyond the distal end 60 of the sleeve 56 when the shaft is in the extended position, thus exposing the distal end 76 of the shaft 70 outside the sleeve 56. This latter feature may be advantageous when the probe 50 is configured with an imaging component 86 at the distal end 76 of the shaft 70. Coupling an imaging component 86 to the distal end of the shaft, or otherwise to the distal end of the probe, may assist in the process of delivering HIFU therapy to the patient.

The imaging component 86 is preferably adapted to produce an image of a portion of the patient's body that includes the treatment site receiving the HIFU energy. Conventional imaging technologies may be used. The image may help guide the delivery of HIFU energy to the treatment site. In one aspect, the imaging component may be configured to use reflected ultrasound energy to produce the image of the portion of the patient's body. Diagnostic ultrasound uses ultrasound energy at a much lower power density so as not to damage tissue. Reflected ultrasound energy can measure tissue forms and densities at various depths in the patient's body.

Alternatively, the imaging component 86 may be configured to use reflected light to produce a visual image of a portion of the patient's body. Light-based imaging technologies may include elements such as fiber optic transmission and reception of light, lenses (as needed), and/or electronic charge-coupled devices (CCDs) that can receive and measure reflected light to produce an image.

Where reflected ultrasound energy is used to produce an image, the emission and reception of diagnostic ultrasound energy should be synchronized with the transmission of HIFU energy so as not to obscure the image obtained by the imaging component 86. Technologies for synchronizing imaging and HIFU pulses are available in the art. See, e.g., U.S. Patent Application Publication No. 2006/0264748, titled "Interference-Free Ultrasound Imaging During HIFU Therapy, Using Software Tools," by Shahram Vaezy et al., the disclosure of which is incorporated by reference herein.

Additionally, imaging technologies may be used to provide real-time two-dimensional or three-dimensional viewing of the target site, as well as blood flow color imaging (Doppler) and temperature change quantifications of the target tissue, using ultrasound back scatter information obtained from either the HIFU transducer or the imaging component.

Figure 5A:
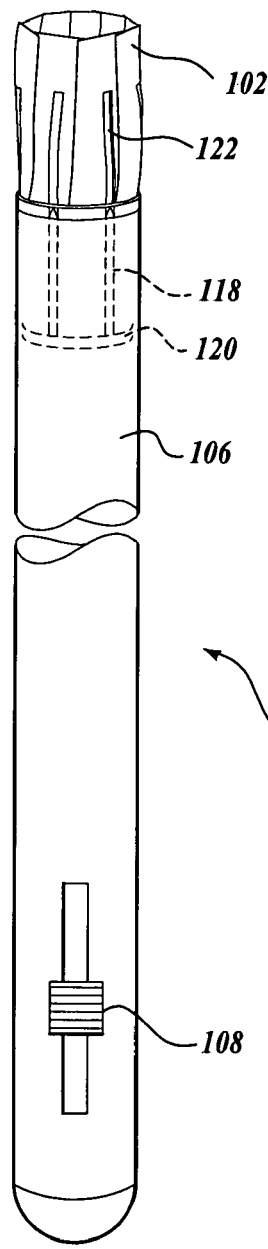
FIGS. 5A and 5B illustrate an implementation of the invention with a collapsible HIFU therapy transducer.
Figure 5B:
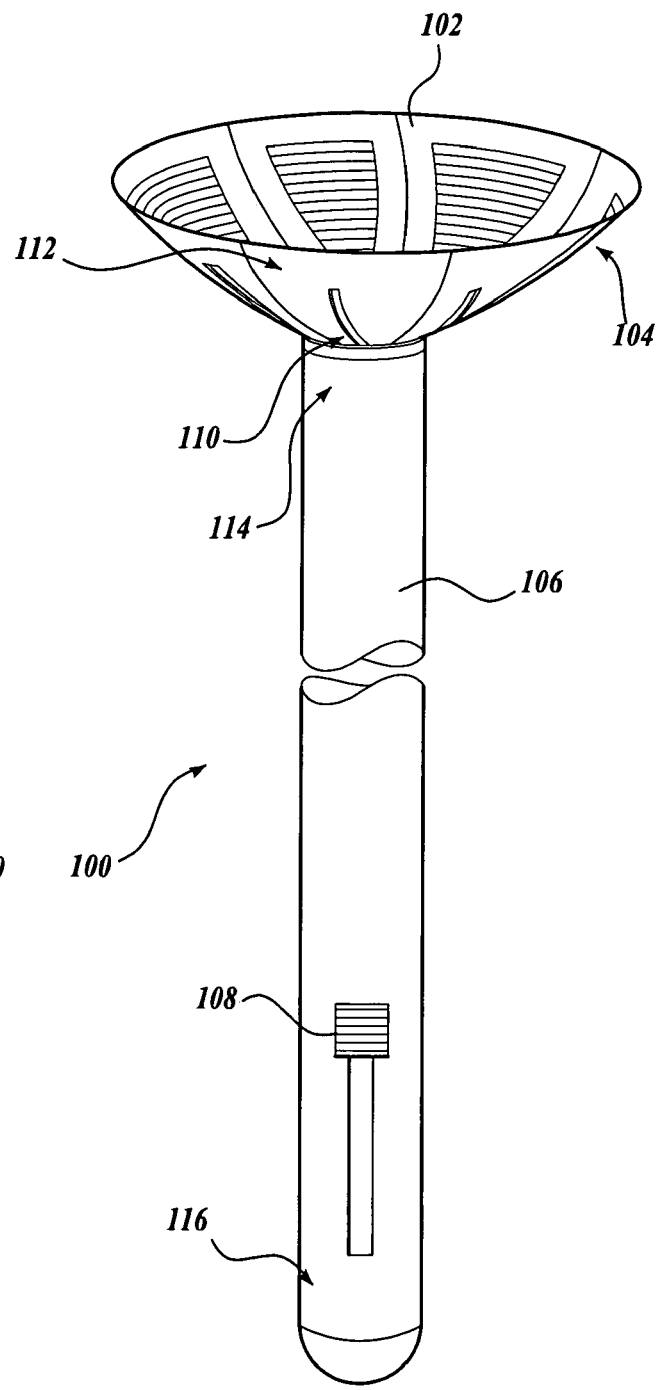

FIGS. 5A and 5B illustrate an implementation of a probe 100 with features similar to those shown and described with respect to FIGS. 1-4, including a plurality of leaves 102 that can be deployed to collectively provide a bowl-shaped HIFU transducer 104. As with the previously described implementations, the probe 100 further includes a sleeve 106 disposed around a shaft within the sleeve. An actuator, such as the button 108, is connected to the shaft to assist in sliding the shaft from a retracted position, as shown in FIG. 5A, to an extended position, as shown in FIG. 5B.

In contrast to the previously described implementation, the leaves 102 are coupled to the sleeve 106. More specifically, each leaf 102 has a proximal end 110 and a distal end 112. The proximal end 110 of each leaf is coupled to the distal end 114 of the sleeve 106. Furthermore, the proximal end 116 of the sleeve 104 may have a section adapted for positioning the distal end 114 at a desired location within a patient's body when the probe 100 is inserted into the patient.

As further depicted in dotted line in FIG. 5A, a plurality of spines 118 may be coupled to the distal end 120 of the shaft within the sleeve 106. When the shaft is in the retracted position, as shown in FIG. 5A, the spines 118 are held within the sleeve 106. The leaves 102 are constructed such that they can overlap one another in a collapsed configuration as shown, where the leaves 102 are capable of being grouped together to occupy a smaller space. For example, as shown in FIG. 5A, the group of leaves 102 may occupy a space having a diameter that is equal to or smaller than the diameter of the sleeve 106. Having the leaves in a collapsed state facilitates insertion of the probe 100 into a patient's body. After the probe 100 is inserted into the intended cavity of a patient's body, the leaves 102 may be deployed using a deployment mechanism, namely, the spines 118, to direct the distal end 112 of each leaf in a radially outward direction to a desired position to provide the bowl-shaped HIFU transducer 104.

Thus, in operation, activation of the deployment mechanism for FIGS. 5A and 5B comprises sliding the shaft within the sleeve 106 toward the extended position, as depicted in FIG. 5B. As the shaft is slid within the sleeve, the spines 118 emerge from the sleeve 106 and slide within grooves 122 defined in each of the leaves 102. As the spines 118 progressively enter the grooves 122, the spines 118 direct the distal end 112 of each of the leaves 102 in a radially outward direction. The spines 118 also provide support to the leaves 102 when the plurality of leaves are deployed. Pulling the shaft into the sleeve 106 toward the retracted position withdraws the spines 118 from the grooves 122, which allows the leaves 102 to collapse to the state shown in FIG. 5A.

The spines 118 may be constructed of a suitable material capable of providing support to the leaves 102 when the shaft is extended and the leaves are deployed. The spines 118 may be configured to exert an outwardly directed bias force on the leaves 102 when the shaft is extended and the spines 118 fill the grooves 122. The spines 118 are constructed to hold the leaves 104 in the deployed state, as shown in FIG. 5B. If desired, one or more stops may be defined in the distal end 114 of the sleeve 106 to engage the leaves 102 once the leaves have reached the deployed position. The outwardly-directed bias force of the spines 118 may derive from a natural characteristic of the materials used to construct the spines, such as a spine formed of a material having an outwardly-directed curve in a resting state outside the sleeve 106, which is flexible to bend to a straight non-resting state inside the sleeve 106. Alternatively, a mechanism, such as a spring, may be configured with the spines 118 to bear against the spines 118 and direct the leaves in a radially outward direction when deployed.

In another alternative implementation, a deployment mechanism comprised of springs having a first end coupled to the shaft and a second end disposed within the leaf, may be used. An implementation using springs for deployment may be visualized using the drawings in FIGS. 3A-3C, wherein the grooves 80 are filled with the second end of a spring, as described, instead of being guided by pins 78 in the sleeve 56. In this case, the second end of the springs need not be disposed at an angle as the grooves 80 are depicted. As the shaft within the sleeve 56 is slid upward to an extended position, as shown in FIG. 3C, the second end of the springs emerges from the sleeve 56 and exerts an outward bias to direct the distal end of the leaves 54 in a radially outward direction. Similarly, retracting the shaft within the sleeve 56 pulls the leaves 54 with the springs into the sleeve 56, wherein the leaves and springs are held, as shown in FIG. 3A.

In yet another implementation, a portion of the leaves, such as the leaves 102 shown in FIG. 5B, may be formed of an energy-activated shape memory alloy. The deployment mechanism of the leaves 102 in this implementation includes a coupling that connects the shape memory alloy to an energy source. Activation of the deployment mechanism comprises delivering energy from the energy source to the shape memory alloy in each leaf that causes the shape memory alloy to take a predefined shape in which the distal end of the leaves 102 are directed radially outward to provide a bowl-shaped HIFU transducer 104.

A typical shape memory alloy is made of nickel and titanium and is known for its flexibility as well as shape changing properties. The alloy dynamically changes its internal structure at certain temperatures. Structures formed with a shape memory alloy, such as the leaves 102, can be deformed at room temperature, and when the shape member alloy is heated, the alloy causes the structure to shift to a predefined shape. For example, shape memory alloys may contract when heated and then be easily stretched out again as they return to their original temperature. Energy-driven heating and cooling of a shape memory alloy can be accomplished quite quickly.

In the context of the present invention, a probe, such as the probe 100 shown in FIG. 5B (without spines 118 shown in FIG. 5A), may include a plurality of leaves 102 having a proximal end 110 coupled to the probe. Some or all of each leaf 102 may be formed of a shape memory alloy. As energy from an energy source within the probe is delivered to the shape memory alloy of the leaves, the leaves flex in a radially outward direction to provide the HIFU therapy transducer 104, as shown. In an implementation where spines 118 are used, the spines may be formed of a shape memory alloy which, being activated by the application of energy to the alloy, cause each of the spines 118 to flex in a radially outward direction, thus placing the leaves 102 in a deployed state. In such implementations, the spines 118 may or may not retract within grooves 122, as shown in FIG. 5A. Where the spines 118 do not retract, the leaves 102 are still capable of collapsing into a group, as shown in FIG. 5A, when the shape memory alloy of the spines 118 is not activated by the energy source.

Figure 6A:
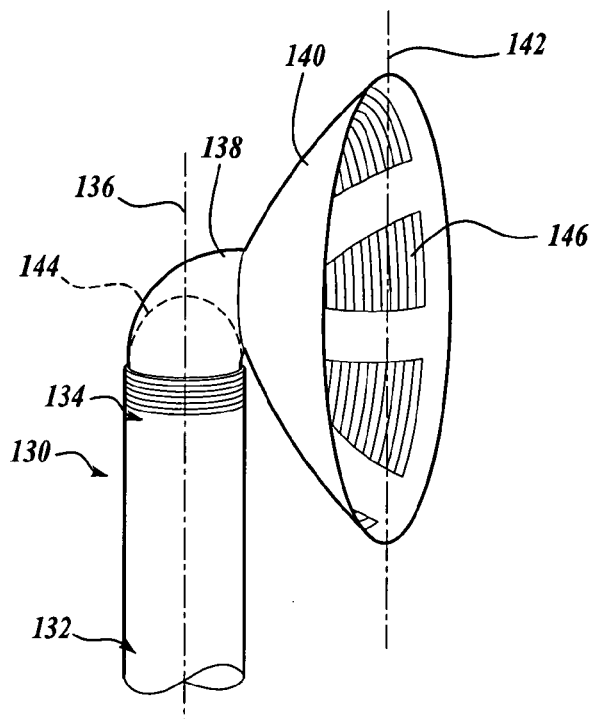
FIGS. 6A and 6B illustrate an implementation of the invention with a flexible material coupling a HIFU therapy transducer to a probe.
Figure 6B:
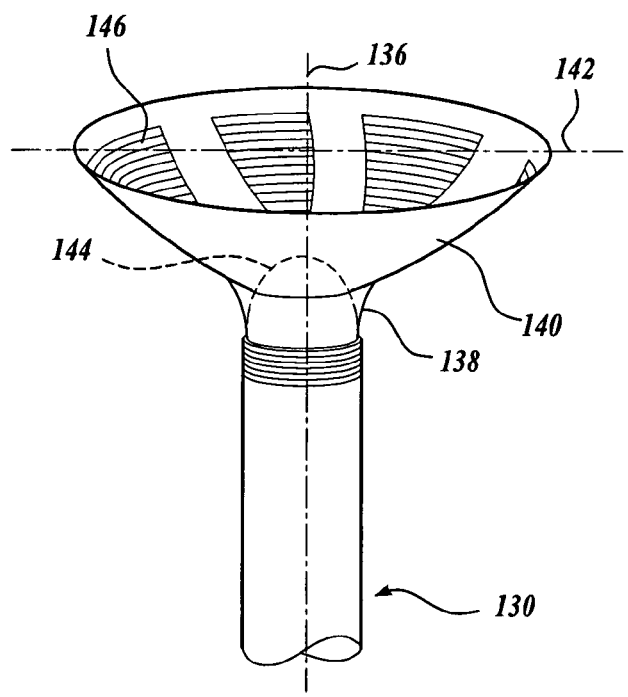

Turning now to FIGS. 6A and 6B, another implementation constructed in accordance with the present invention comprises an elongate probe 130 having a proximal end 132, a distal end 134, and a longitudinal axis 136 extending therebetween. As with other implementations herein, the proximal end 132 of the probe 130 may have a section adapted for positioning the distal end 134 of the probe at a desired location within a patient's body when the probe 130 is inserted into the patient.

The distal end 134 of the probe 130 is fitted with a flexible material 138 that couples a HIFU therapy transducer 140 to the probe 130. The HIFU therapy transducer 140 has an aperture of a size sufficient to direct therapeutic HIFU energy to a treatment site in the patient. For reference purposes, the HIFU therapy transducer 140 has a major axis 142 extending across its face.

In a resting state, as shown in FIG. 6B, the flexible material 138 couples the transducer 140 to the probe 130 in a therapy position wherein the major axis 142 of the transducer is non-parallel to the longitudinal axis 136 of the probe. To facilitate insertion of the probe 130 in a patient's body, e.g., through the vaginal introitus, the flexible material 138 is configured to stretch and allow the transducer 140 to be drawn to the side of the probe 130 to an insertion position as shown in FIG. 6A. In the insertion position, the major axis 142 of the transducer 140 is generally parallel to the longitudinal axis 136 of the probe 130. This allows the largest dimension of the transducer 140 to be in the sagittal axis of the vaginal introitus. The flexible material 138, thus stretched, exhibits a bias to return toward its resting state as shown in FIG. 6B. After the probe 130 has been inserted into the intended cavity of a patient's body, such as the vaginal cavity, the transducer 140 is released from the insertion position and allowed to return to the therapy position shown in FIG. 6B.

If desired, an actuator may be coupled to the HIFU therapy transducer 140 to draw the transducer 140 to the side of the probe 130 while the probe is either being inserted into the patient or withdrawn from the patient. The actuator may also be manipulated to deploy the transducer 140 to the therapy position shown in FIG. 6B. Suitable actuators include, but are not limited to, a cable and/or a latch that can pull, push, and/or hold the transducer in an insertion position as shown in FIG. 6A or in a therapy position as shown in FIG. 6B. In at least one implementation, manipulating the actuator to deploy the transducer 140 may simply involve releasing the transducer and allowing the flexible material 138 to place the transducer in a therapy position. In another implementation, the actuator may actively move the transducer 140 to the desired therapy position.

As with other implementations previously described, the distal end 134 of the probe 130 may include an imaging component 144 adapted for producing an image of a portion of the patient's body when the probe 130 has been inserted in the patient. Preferably, the image produced by the imaging component includes the treatment site receiving the HIFU energy from the transducer 140 to help guide the delivery of the HIFU energy to the treatment site. In one implementation, the imaging component may be configured to use reflected ultrasound energy to produce the image of the portion of the patient's body. In an alternative implementation, the imaging component may be configured to use reflected light to produce the image. In either case, the image produced by the imaging component may further include a portion of the HIFU therapy transducer 140 to assist in positioning the transducer 140 within the patient's body and in monitoring the HIFU therapy occurring at the treatment site.

In a suitable implementation, the flexible material 138 may be comprised of a resilient, non-metal material, such as a medical grade plastic, rubber, or silicon. In an alternative implementation, the flexible material 138 may be comprised of a shape memory alloy having a stretched state or resting state dependent on energy activation of the alloy. The shape memory alloy may be activated to assume a predefined shape based on energy supplied to the alloy which typically heats the alloy and causes the change in shape. Details regarding the structure and use of shape memory alloys have been discussed earlier herein.

Also, as with earlier described implementations, an active element 146 may be disposed on the HIFU therapy transducer 140, wherein the active component is operable to generate the HIFU energy that the transducer 140 directs to the treatment site. Alternatively, the HIFU therapy transducer 140 may be configured with a surface that reflects HIFU energy toward the treatment site. The HIFU energy in this latter implementation may be received from a source that is remote from the transducer 140. Materials, such as a reflective Mylar, capable of reflecting ultrasound energy that is incident thereon, are known in the art.

In yet another implementation of an apparatus constructed according to the present invention, a probe 160, as shown in FIGS. 7A and 7B, may be used to treat pathologies in a patient's body. To facilitate insertion of the probe 160 in the patient, the probe 160 is configured with a HIFU therapy transducer formed of one or more inflatable bladders.

As with prior implementations, the elongate probe 160 has a proximal end 164 and a distal end 166. The proximal end 164 preferably has a section adapted for positioning the distal end 166 of the probe at a desired location when the probe 160 is inserted into a patient's body. The distal end 166 of the probe 160 is fitted with a flexible material having one or more inflatable bladders that, when inflated, provide the HIFU therapy transducer 162. The transducer 162 has an aperture of a size sufficient to direct a focused beam of therapeutic HIFU energy to a treatment site in a patient. The inflatable bladders may be constructed of an expandable material, such as (but not limited to) rubber or silicon.

The one or more inflatable bladders 168 extend radially outward from the distal end 166 of the probe 160. The bladders 168 are not inflated until after the probe is inserted into the intended cavity of the patient's body, such as through the vaginal introitus into the vaginal cavity. After insertion, the bladders 168 are inflated to form and provide lateral support to the HIFU therapy transducer 162 within the patient's body. When inflated, the transducer 162 has an aperture that is larger than the diameter of the probe 160. Appropriate conduits for delivering a pressurized fluid, such as a liquid or gas, to the inflatable bladders 168 are provided within the probe 160 and coupled to the bladders 168. Likewise, conduits are provided to conduct the fluid away from the bladders 168 when the bladders are deflated. If desired, the fluid (liquid or gas) may be circulated to and from the bladders 168 and cooled to help manage the temperature of the transducer 162 and/or tissue adjacent to the transducer 162 when HIFU therapy is being applied.

As further depicted in FIG. 7B, the flexible material forming the HIFU therapy transducer 162 has a front surface 170 adapted to direct HIFU energy to the treatment site in the patient when the probe 160 is inserted and the bladders 168 are inflated.

In the implementation illustrated in FIGS. 7A and 7B, the bladders 168 comprise one or more inflatable channels that extend radially outward from the distal end 166 of the probe 160. The front face 170 of the flexible material extends between the inflatable channels 168.

If desired, the inflatable channels 168 may terminate in an inflatable ring 172 that forms an outer edge 174 of the HIFU therapy transducer 162. The ring 170, when inflated, provides further support to the HIFU therapy transducer 162 and maintains the aperture of the transducer for delivery of HIFU therapy to the patient. When inflated, the diameter of the ring 172, measured as a cross-section of the ring, is larger than the diameter of the probe 160, measured at the distal end 166 of the probe.

In FIG. 7B, the front surface 170 of the flexible material is shown with one or more active elements 176 that are operable to generate HIFU energy that is directed by the transducer 162 to the treatment site in the patient. As noted earlier, HIFU generating elements are known in the art. Conduits for providing energy to the active element 176 are provided within the probe 160. Alternatively, the front surface 170 may be configured with a material that reflects HIFU energy toward the treatment site. As with other implementations described herein, the HIFU energy may be received from a source that is remote from the flexible material.

Additionally, as with other implementations described herein, the distal end 166 of the probe 160 may further include an imaging component 176 adapted for producing an image of a portion of the patient's body that includes the treatment site. Imaging of the patient in this manner may help guide the delivery of HIFU energy to the treatment site. The imaging component 176 may be configured to use reflected ultrasound energy or reflected light to produce the image, as described earlier herein. The image produced by the imaging component 176 may further include a portion of the HIFU therapy transducer 162 to assist in positioning the transducer within the patient's body and in monitoring HIFU therapy being delivered at the treatment site.

FIG. 8 illustrates an implementation of a probe 180 that is likewise fitted with a flexible material having an inflatable bladder that, when inflated, provides a HIFU therapy transducer 182. The transducer 182 may include one or more active elements 184, as shown, or provide a reflective mirror surface that reflects HIFU energy toward the treatment site. In contrast to the implementation with inflatable channels 168 shown in FIGS. 7A and 7B, FIG. 8 depicts an implementation with a single inflatable bladder 186 that, when inflated, is capable of providing HIFU therapy to a patient. To facilitate insertion of the probe 180 in the patient's body, the bladder 186 is not inflated until after the probe is inserted in the intended cavity of the patient's body. The bladder 186, when inflated, forms and provides lateral support to the HIFU therapy transducer 182.

Figure 9A:
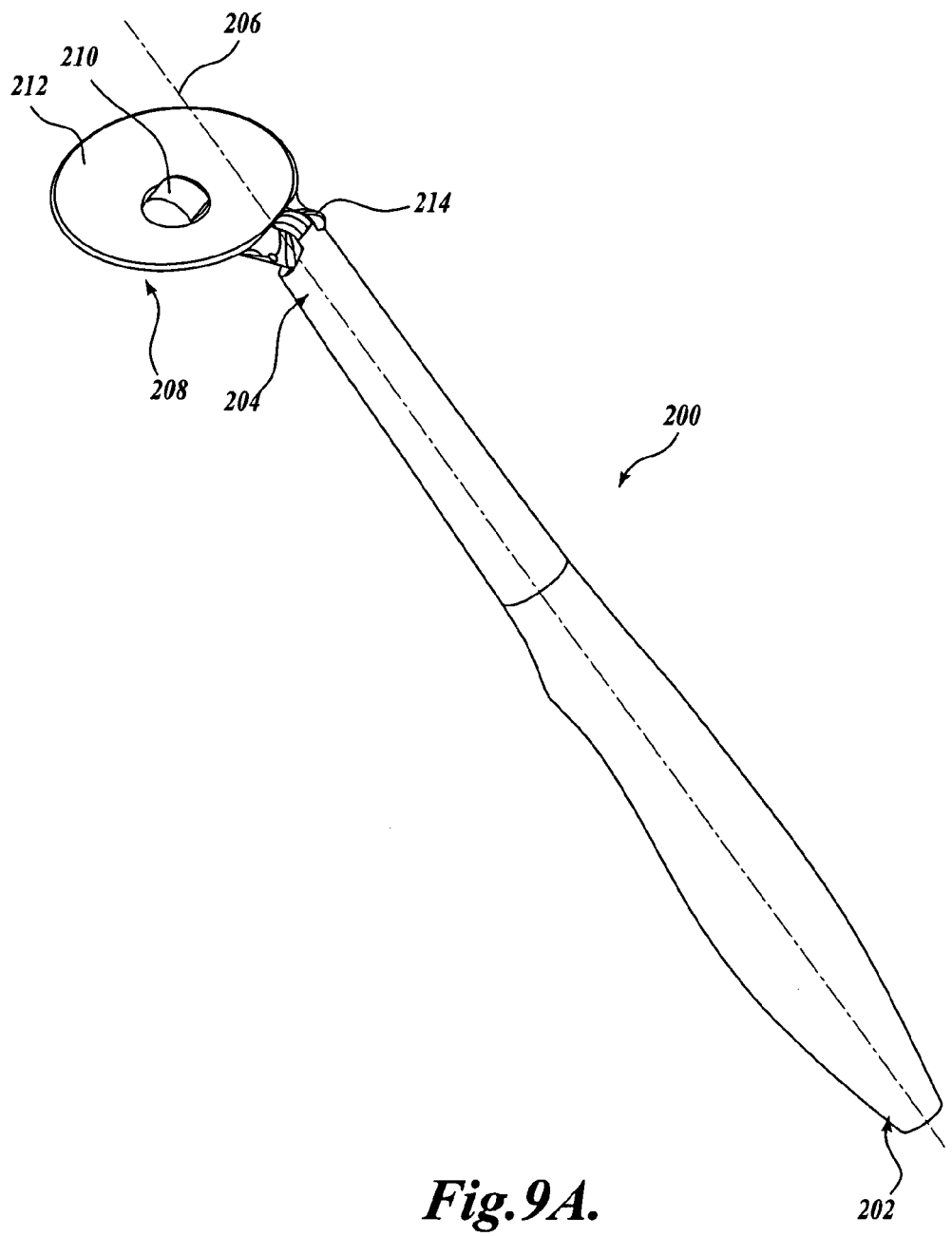
FIGS. 9A and 9B illustrate further aspects of an implementation of the invention with an imaging component and HIFU therapy transducer as a unit configured to rotate about a hinge, where the imaging component is disposed within the interior of the HIFU therapy transducer.
Figure 9B:
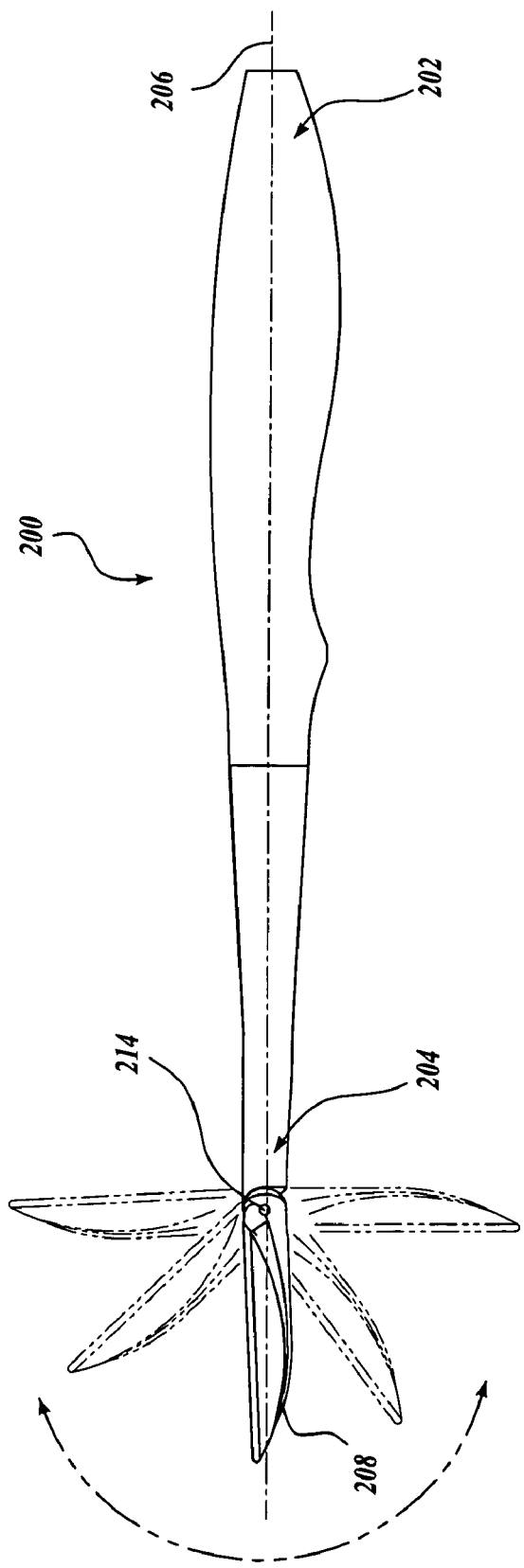

Turning now to FIGS. 9A and 9B, an apparatus for delivering HIFU energy to a treatment site internal to a patient's body is shown in accordance with another implementation of the invention. The apparatus includes an elongate probe 200 having a proximal end 202, a distal end 204, and a longitudinal axis 206 extending therebetween. The proximal end 202 of the probe 200 preferably has a section adapted for positioning the distal end 204 of the probe at a desired location within the patient's body.

Further depicted in FIGS. 9A and 9B is a support structure 208 having an imaging component 210 and a HIFU therapy transducer 212 disposed thereon. A hinge 216 connects the support structure 208 to the distal end 204 of the probe 200.

The imaging component 210 is adapted for producing an image of a portion of the patient's body that includes the treatment site, while the HIFU therapy transducer is adapted for delivering HIFU energy to the treatment site. The HIFU therapy transducer has an aperture of a size sufficient to direct therapeutic HIFU energy to the treatment site and is disposed on the support structure 208 in defined relation to the imaging component 210. In the particular implementation shown, the HIFU therapy transducer 212 is bowl-shaped, and the imaging component 210 is disposed within the interior of the therapy transducer 212.

To facilitate insertion of the probe 200 in the patient's body, e.g., through the vertical axis of the vaginal introitus, the support structure 208 is capable of rotating about the hinge 214 to an insertion position generally parallel to the longitudinal axis 206 of the probe 200, as shown in FIG. 9B. In at least one implementation, the dimension of the therapy transducer 212 in its insertion position and measured perpendicular to the longitudinal axis 206 of the probe is smaller than the dimension of the transducer 212 measured parallel to the longitudinal axis 206. The hinge 214 provides an articulation that enables the imaging and therapy transducers 210, 212 as a unit to be positioned relative to the treatment site in the patient's body. In this implementation, the alignment of the imaging and HIFU therapy is maintained, thus maintaining the focal range of the HIFU therapy field in the same region on the image plane. Advantageously, this region can be determined and calibrated at the factory. Thereafter, as a result, software control of HIFU transducer will be simpler.

After insertion of the distal end 204 of the probe 200 in a patient's body, the support structure 208 is capable of rotating about the hinge 214 to a position non-parallel to the longitudinal axis 206 of the probe 200, as may be desired to effectively aim the HIFU energy from the therapy transducer 212 to the treatment site in the body. By rotation, the HIFU therapy transducer 212 can also be placed in a better position for coupling to a bodily structure, such as the uterine cervix of a female patient.

Figure 10A:
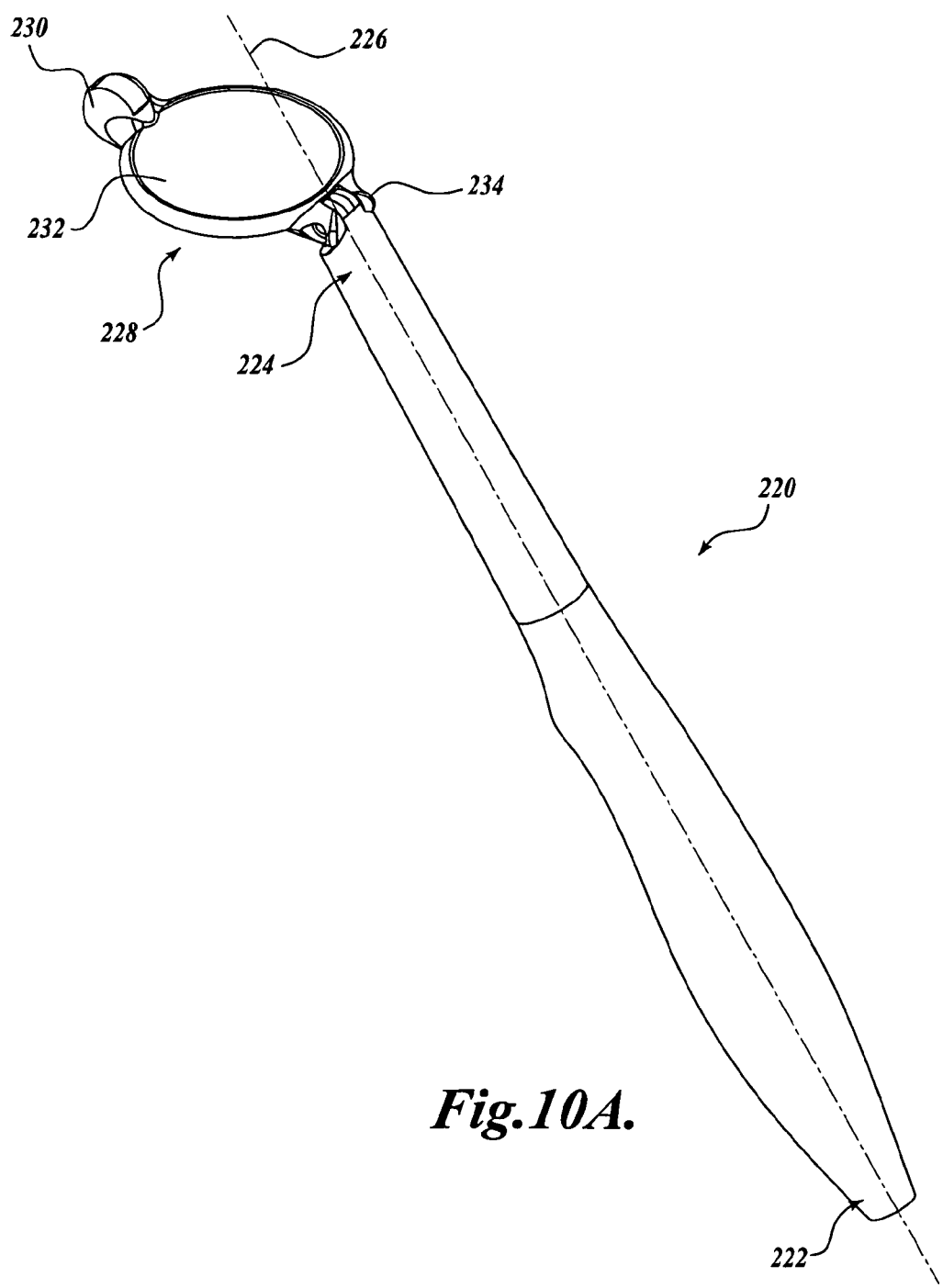
FIGS. 10A and 10B illustrate further aspects of an implementation of the invention similar to the implementation shown in FIGS. 9A and 9B, where the imaging component is disposed to the exterior of the HIFU therapy transducer.
Figure 10B:
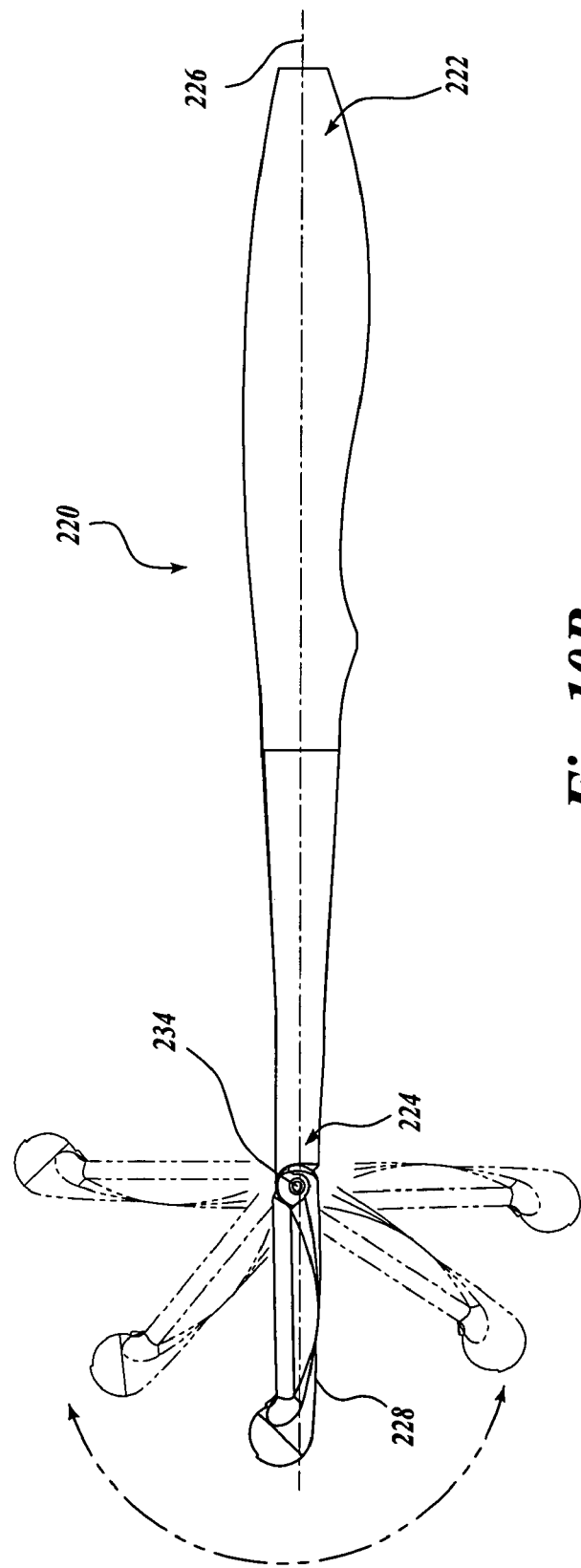

Lastly, FIGS. 10A and 10B depict an elongate probe 220 having features similar to those shown in the probe 200 of FIGS. 9A and 9B. The probe 220 has a proximal end 222, a distal end 224, and a longitudinal axis 226 extending therebetween. A support structure 228 bearing an imaging component 230 and a HIFU therapy transducer 232 is rotatable about a hinge 234 connected to the distal end 224 of the probe 220.

In contrast to the probe 200 shown in FIGS. 9A and 9B, the imaging component 230 shown in FIGS. 10A and 10B is disposed on the support structure 228 to the exterior of the HIFU therapy transducer 232. Having the imaging transducer to the exterior of the therapy transducer in some circumstances may provide a more advantageous angle for imaging the treatment site and the effects of the HIFU therapy being delivered thereto.

In a suitable implementation, the imaging component 230 as well as the imaging component 210 may be configured to use reflected ultrasound energy to produce an image of a portion of the patient's body. In other suitable implementations, the imaging component 230 and/or the imaging component 210 may be configured to use reflected light to produce a visual image. Where reflected ultrasound energy is used to produce the image, an implementation of the invention may use the same transducer, such as the transducers 212 and/or 232, to perform both the imaging and delivery of HIFU therapy. Appropriate synchronization of the imaging and HIFU pulses will be desired. Nevertheless, in such cases, an imaging component 210, 230 separate from the therapy transducer 212, 232 is not necessary. If a portion of the HIFU therapy transducer is shown in the image, the image may further assist in positioning the HIFU therapy transducer within the patient's body and in monitoring the delivery of HIFU therapy at the treatment site.

An overall control system for the above-described probes can be implemented using computer hardware and/or software. A control system may provide tools for clinicians to program a treatment strategy for a specific region of interest in the body. The tools may include setting various focal lengths to treat a two-dimensional or three-dimensional region in the tissue, setting an appropriate power level for excitation of the HIFU transducer to obtain a desired intensity at the focus (either for a single element HIFU or a multi-element HIFU transducer) based on expected attenuation of the tissue between the HIFU transducer and the focus, setting a duration of the HIFU application, setting a threshold for power above which the system should shut down for safety purposes, and setting a duty cycle of the HIFU exposure with respect to ultrasound image acquisition. An interface may also provide tools for the clinician to override the computer plan and design a treatment plan based on their discretion. The interface may continually update the clinician of the stage of the treatment and the next steps to be taken, as well as advise whether the plan should proceed or be altered. Finally, the interface may continually interrogate the acoustic path (pre- and post-focal) for bone and gas interfaces that could potentially result in excessive energy deposition, leading to potential undesired tissue damage.

For purposes of example only, various implementations have been described above for treating pathologies of the female reproductive system where necrosis of a region of tissue has a therapeutic effect. By way of example, and not by limitation, these implementations can be used to treat uterine fibroids, adenomyoma of the uterus, adenomyosis of the uterus, endometrial polyps, endometrial ablation to achieve reduction or elimination of menstrual flow, endometrial hyperplasia, cornual pregnancy, benign ovarian cysts, pelvic endometriosis, ectopic pregnancy, and malignant lesions of the pelvic organs, whether primary or metastatic.

As may be appreciated from the various implementations described herein, there are a variety of features and advantages obtained when constructing a probe in accordance with the present invention. Furthermore, although the invention has been described in connection with certain depicted implementations, those of ordinary skill will recognize that one or more features of a particular implementation described herein may be used in another implementation for similar advantage. Accordingly, it is not intended that the scope of the invention in any way be limited by the precise forms described above, but instead be determined by reference to the claims that follow and equivalents thereto.

While illustrative embodiments have been illustrated and described, it will be appreciated that various changes can be made therein without departing from the spirit and scope of the invention.

The embodiments of the invention in which an exclusive property or privilege is claimed are defined as follows:

1. An apparatus for delivering high intensity focused ultrasound (HIFU) energy to a treatment site internal to a patient's body, comprising:
   an elongate probe having a proximal end and a distal end, the proximal end of the probe having a section adapted for positioning the distal end of the probe at a desired location within the patient's body,
   wherein the distal end of the probe is fitted with a flexible material having one or more inflatable bladders that, when inflated, extend outward from the distal end of the probe and position the flexible material to form a HIFU therapy transducer with one or more active elements on a front surface of the flexible material, the one or more active elements being configured to generate therapeutic HIFU energy and direct the therapeutic HIFU energy to the treatment site, and
   wherein, to facilitate insertion of the probe in the patient's body, the bladders are configured to be inflated after the probe is inserted in the patient's body.

2. The apparatus of claim 1, wherein, when inflated, the bladders provide lateral support to the HIFU therapy transducer and the transducer has an aperture that is larger than a diameter of the distal end of the probe.

3. The apparatus of claim 1, wherein the bladders, when not inflated, occupy a space having a diameter smaller than the diameter of the HIFU therapy transducer when the bladders are inflated.

4. The apparatus of claim 1, wherein the bladders are inflated using a fluid that is circulated to and from the bladders to control a temperature of the HIFU therapy transducer and tissue adjacent to the HIFU therapy transducer when the probe is inserted into the patient.

5. The apparatus of claim 1, wherein the bladders comprise one or more inflatable channels that extend radially outward from the distal end of the probe.

6. The apparatus of claim 5, wherein the inflatable channels terminate in an inflatable ring that forms an outer edge of the HIFU therapy transducer.

7. The apparatus of claim 6, wherein, when inflated, the diameter of the ring is larger than a diameter of the distal end of the probe.

8. The apparatus of claim 1, wherein the distal end of the probe further includes an imaging component configured to produce an image of a portion of the patient's body that includes the treatment site to help guide the delivery of HIFU energy to the treatment site.

9. The apparatus of claim 8, wherein the imaging component is configured to use reflected ultrasound energy to produce the image of the portion of the patient's body.

10. The apparatus of claim 8, wherein the imaging component is configured to use reflected light to produce the image of the portion of the patient's body.

11. The apparatus of claim 8, wherein the image further includes a portion of the HIFU therapy transducer to assist in positioning the HIFU therapy transducer within the patient's body and in monitoring HIFU therapy at the treatment site.

12. A method of delivering high intensity focused ultrasound (HIFU) energy to a treatment site internal to a patient's body, comprising:
- inserting an elongate probe into a patient's body, the elongate probe having a proximal end and a distal end, the proximal end of the probe having a section adapted for positioning the distal end of the probe at a desired location within the patient's body;
- inflating one or more inflatable bladders in connection with the elongate probe such that, when inflated, the inflatable bladders extend outward from the distal end of the probe and position a flexible material to form a HIFU therapy transducer with one or more active elements on a front surface of the flexible material, the one or more active elements being configured to generate therapeutic HIFU energy and direct the therapeutic HIFU energy to the treatment site,
- wherein, to facilitate insertion of the probe in the patient's body, the bladders are inflated after the probe is inserted in the patient's body.

13. The method of claim 12, wherein, when inflated, the bladders provide lateral support to the HIFU therapy transducer and the transducer has an aperture that is larger than a diameter of the distal end of the probe.

14. The method of claim 12, wherein the bladders, when not inflated, occupy a space having a diameter smaller than the diameter of the HIFU therapy transducer when the bladders are inflated.

15. The method of claim 12, wherein inflating the one or more inflatable bladders comprising using a fluid that is circulated to and from the bladders to control a temperature of the HIFU therapy transducer and tissue adjacent to the HIFU therapy transducer when the probe is inserted into the patient.

16. The method of claim 12, wherein inflating the one or ore inflatable bladders comprises inflating one or more inflatable channels that extend radially outward from the distal end of the probe.

17. The method of claim 16, wherein the inflatable channels terminate in an inflatable ring that forms an outer edge of the HIFU therapy transducer and has a diameter that is larger than a diameter of the distal end of the probe.

18. The method of claim 12, further comprising imaging a portion of the patient's body that includes the treatment site to help guide the delivery of HIFU energy to the treatment site, wherein the image further includes a portion of the HIFU therapy transducer to assist in positioning the HIFU therapy transducer within the patient's body and in monitoring HIFU therapy at the treatment site.

19. The method of claim 18, wherein said imaging comprises using reflected ultrasound energy to produce the image of the portion of the patient's body.

20. The method of claim 18, wherein said imaging comprises using reflected light to produce the image of the portion of the patient's body.

* * * * *